US006630124B1

(12) United States Patent
Gozes et al.

(10) Patent No.: US 6,630,124 B1
(45) Date of Patent: Oct. 7, 2003

(54) COMBINATION THERAPY WITH VIP ANTAGONIST

(75) Inventors: Illana Gozes, Ramat Hasharon (IL); Mati Fridkin, Rehovot (IL); Edgar Gelber, Petach Tikva (IL); Terry W. Moody, Germantown, MD (US); Douglas C. Brenneman, Damascus, MD (US)

(73) Assignees: Ramot-University Authority for Applied Research and Industrial Development Ltd., Tel-Aviv (IL); Yeda Research and Development Co. Ltd., Rehovot (IL); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/807,557

(22) PCT Filed: Oct. 15, 1999

(86) PCT No.: PCT/US99/24268

§ 371 (c)(1),
(2), (4) Date: Jan. 9, 2002

(87) PCT Pub. No.: WO00/23096

PCT Pub. Date: Apr. 27, 2000

Related U.S. Application Data

(60) Provisional application No. 60/104,472, filed on Oct. 16, 1998, and provisional application No. 60/104,907, filed on Oct. 20, 1998.

(51) Int. Cl.[7] .................. A61K 51/00; A61M 36/14
(52) U.S. Cl. ............... 424/1.69; 424/1.11; 424/9.1; 530/324; 514/12
(58) Field of Search .................. 424/1.11, 1.41, 424/1.49, 1.53, 1.65, 1.69, 9.1, 9.2; 514/2, 9, 11, 12, 13; 530/300, 315, 324

(56) References Cited

U.S. PATENT DOCUMENTS 5,217,953 A * 6/1993 Gozes et al. ................. 514/12
5,565,424 A * 10/1996 Gozes et al. ................. 514/12
6,239,107 B1 * 5/2001 Gozes et al. ................. 514/14

OTHER PUBLICATIONS

Moody et al (1999), Proceedings of the American Association for Cancer Research, vol. 40, p. 23, #153.*
Gelber et al (2001) , Cancer, vol. 92, pp. 2172–2180.*
Oliver (1997), European Journal of Surgical Oncology, vol. 23, pp. 117–122.*
O'Doherty et al (1997), Journal of Cancer, Vo. 76, Suppl. 1, p. 50, #PO46.*

* cited by examiner

Primary Examiner—Dameron L. Jones
(74) Attorney, Agent, or Firm—Townsend and Townsend and Crew LLP

(57) ABSTRACT

The present invention relates to combination therapy using a pharmaceutical composition comprising a polypeptide which is an antagonist of the vasoactive intestinal polypeptide (VIP) and a chemotherapeutic agent. Methods of using the pharmaceutical composition are also disclosed.

47 Claims, 12 Drawing Sheets

SEQUENCE LISTING

```
<160> NUMBER OF SEQ ID NOS: 8

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence:vasoactive
      intestinal polypeptide (VIP) antagonist
<220> FEATURE:
<221> NAME/KEY: MOD_RES
<222> LOCATION: (1)
<223> OTHER INFORMATION: Xaa = Lys modified by 1-R, where 1-R = H,
      C-1 to C-20 alkyl or C-1 to C-20 acyl
<220> FEATURE:
<221> NAME/KEY: MOD_RES
<222> LOCATION: (17)
<223> OTHER INFORMATION: Xaa = any naturally occurring amino acid or
      amino acid analog or mimetic, provided Xaa is not Met
<220> FEATURE:
<221> NAME/KEY: MOD_RES
<222> LOCATION: (19)
<223> OTHER INFORMATION: Xaa = any naturally occurring amino acid or
      amino acid analog or mimetic
<220> FEATURE:
<221> NAME/KEY: MOD_RES
<222> LOCATION: (28)
<223> OTHER INFORMATION: Xaa = asparaginamide modified by 2-R, where
      2-R = H, C-1 to C-20 alkyl or C1- C20 acyl
```

```
<400> SEQUENCE: 1

Xaa Pro Arg Arg Pro Tyr Thr Asp Asn Tyr Thr Arg Leu Arg Lys Gln
 1               5                  10                  15

Xaa Ala Xaa Lys Lys Tyr Leu Asn Ser Ile Leu Xaa
            20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence:vasoactive
      intestinal polypeptide (VIP) antagonist, NL-hybrid
      VIP antagonist
<220> FEATURE:
<221> NAME/KEY: MOD_RES
<222> LOCATION: (17)
<223> OTHER INFORMATION: Xaa = Nle
<220> FEATURE:
<221> NAME/KEY: MOD_RES
<222> LOCATION: (28)
<223> OTHER INFORMATION: Xaa = asparaginamide

<400> SEQUENCE: 2

Lys Pro Arg Arg Pro Tyr Thr Asp Asn Tyr Thr Arg Leu Arg Lys Gln
 1               5                  10                  15

Xaa Ala Val Lys Lys Tyr Leu Asn Ser Ile Leu Xaa
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence:lipophilic
      vasoactive intestinal polypeptide (VIP)
      antagonist, S-NL-hybrid VIP antagonist,
      stearyl-Nle-VIP-hybrid (SNH)
<220> FEATURE:
<221> NAME/KEY: MOD_RES
<222> LOCATION: (1)
<223> OTHER INFORMATION: Xaa = stearyl-Lys, Lys modified by
      CH-3(CH-2)-16CO-
<220> FEATURE:
<221> NAME/KEY: MOD_RES
<222> LOCATION: (17)
<223> OTHER INFORMATION: Xaa = Nle
<220> FEATURE:
<221> NAME/KEY: MOD_RES
<222> LOCATION: (28)
<223> OTHER INFORMATION: Xaa = asparaginamide

<400> SEQUENCE: 3

Xaa Pro Arg Arg Pro Tyr Thr Asp Asn Tyr Thr Arg Leu Arg Lys Gln
 1               5                  10                  15

Xaa Ala Val Lys Lys Tyr Leu Asn Ser Ile Leu Xaa
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence:vasoactive
      intestinal polypeptide (VIP) antagonist, S-hybrid
      VIP antagonist
<220> FEATURE:
<221> NAME/KEY: MOD_RES
<222> LOCATION: (1)
<223> OTHER INFORMATION: Xaa = stearyl-Lys, Lys modified by
```

```
        CH-3(CH-2)-16CO-
<220> FEATURE:
<221> NAME/KEY: MOD_RES
<222> LOCATION: (28)
<223> OTHER INFORMATION: Xaa = asparaginamide

<400> SEQUENCE: 4

Xaa Pro Arg Arg Pro Tyr Thr Asp Asn Tyr Thr Arg Leu Arg Lys Gln
 1               5                  10                  15

Met Ala Val Lys Lys Tyr Leu Asn Ser Ile Leu Xaa
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence:vasoactive
      intestinal polypeptide (VIP) antagonist
<220> FEATURE:
<221> NAME/KEY: MOD_RES
<222> LOCATION: (1)
<223> OTHER INFORMATION: Xaa = Lys modified by C-1 to C-20 alkyl
<220> FEATURE:
<221> NAME/KEY: MOD_RES
<222> LOCATION: (17)
<223> OTHER INFORMATION: Xaa = Nle
<220> FEATURE:
<221> NAME/KEY: MOD_RES
<222> LOCATION: (28)
<223> OTHER INFORMATION: Xaa = asparaginamide

<400> SEQUENCE: 5

Xaa Pro Arg Arg Pro Tyr Thr Asp Asn Tyr Thr Arg Leu Arg Lys Gln
 1               5                  10                  15

Xaa Ala Val Lys Lys Tyr Leu Asn Ser Ile Leu Xaa
            20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence:vasoactive
      intestinal polypeptide (VIP) antagonist

<400> SEQUENCE: 6

Lys Pro Arg Arg Pro Tyr Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence:vasoactive
      intestinal polypeptide (VIP)
<220> FEATURE:
<221> NAME/KEY: MOD_RES
<222> LOCATION: (28)
<223> OTHER INFORMATION: Xaa = asparaginamide

<400> SEQUENCE: 7

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Xaa
```

-continued

```
                    20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence:vasoactive
      intestinal polypeptide (VIP) antagonist
<220> FEATURE:
<221> NAME/KEY: MOD_RES
<222> LOCATION: (1)
<223> OTHER INFORMATION: Xaa = Lys modified by 1-R, where 1-R = H,
      C-1 to C-20 alkyl or C-1 to C-20 acyl
<220> FEATURE:
<221> NAME/KEY: MOD_RES
<222> LOCATION: (17)
<223> OTHER INFORMATION: Xaa = Leu, Val or Phe
<220> FEATURE:
<221> NAME/KEY: MOD_RES
<222> LOCATION: (19)
<223> OTHER INFORMATION: Xaa = Leu, Nle or Phe
<220> FEATURE:
<221> NAME/KEY: MOD_RES
<222> LOCATION: (28)
<223> OTHER INFORMATION: Xaa = asparaginamide modified by 2-R, where
      2-R = H, C-1 to C-20 alkyl or C1-C20 acyl

<400> SEQUENCE: 8

Xaa Pro Arg Arg Pro Tyr Thr Asp Asn Tyr Thr Arg Leu Arg Lys Gln
 1               5                  10                  15

Xaa Ala Xaa Lys Lys Tyr Leu Asn Ser Ile Leu Xaa
            20                  25
```

COMBINATION THERAPY WITH VIP ANTAGONIST

CROSS-REFERENCES TO RELATED APPLICATIONS

This application is a 371 of PCT/US99/24268, filed Oct. 15, 1999 which claims priority to U.S. Provisional Patent Application Ser. No. 60/104,472, filed Oct. 16, 1998, and U.S. Provisional Patent Application Ser. No. 60/1104,907, filed Oct. 20, 1998, all the disclosures of which are hereby incorporated by reference in their entirety for all purposes.

FIELD OF THE INVENTION

The present invention relates generally to cancer treatment. More particularly, the present invention relates to combination therapy using a polypeptide which is an antagonist of the vasoactive intestinal polypeptide (VIP) and a chemotherapeutic agent, preferably in a pharmaceutical composition.

BACKGROUND OF THE INVENTION

Vasoactive intestinal polypeptide (VIP) is a widely distributed peptide hormone which mediates a variety of physiological responses including gastrointestinal secretion, relaxation of gastrointestinal vascular and respiratory smooth muscle, lipolysis in adipocytes, pituitary hormone secretion, and excitation and hyperthermia after injection into the central nervous system. Vasoactive intestinal peptide is a 28 amino acid peptide with an amidated C-terminus, the peptide results from post transnational processing of a hormone composed of 170 amino acid residues. The VIP peptide has been shown to contain at least two functional regions, a region involved in receptor specific binding and a region involved in biological activity (Gozes and Brenneman, *Molecular Neurobiology*, 3:201–236 (1989)).

A most striking function of the 28 amino acid peptide, vasoactive intestinal peptide is the ability to promote embryonic growth (see, Gressens, P. et al., *Nature*, 362:1558–8 (1993)). VIP is secreted by nerve endings, immune cells, and by some neoplastic cells (see, Gozes, I. et al., *Current Medicinal Chemistry* in press (1999)). Together with its physiological actions, VIP may exert stimulating and trophic effects on neoplastic cells from neuroblastoma (see, Wollman, Y. et al., *Brain Res.*, 624:339–41 (1993)), breast (Zia, H. et al., *Cancer Res.*, 56:3486–9 (1996)) lung (see, Moody, T. W. et al, *Proc. Natl., Acad. Sci. USA* 90:4345–9 (1993)) and colon cancer (see, Gozes, I. et al., *C. Proceedings of the 15th World Congress of Collegium Internatzonale Chirugiae* 819 (1996)), inducing its own receptors by feedback mechanisms. In neuroblastoma, the most common solid malignancy in young children, VIP has been shown to have the dual effect of either inducing differentiation or stimulating cell division, depending on the cell line and the time of application. In one human neuroblastoma cell line (I), VIP produced dose-dependent stimulation of mitosis (see, Wollman, Y. et al., *Brain Res.*, 624:339–41 (1993)). In contrast, in the mouse neuroblastoma cell line Neuro2a, VIP inhibited proliferation at concentrations as low as $10^{-13}$ M and $10^{-10}$ M, respectively. Similarly, in lung cancer, using growth in soft agar as an index of cancer proliferation, VIP induced growth and VIP antagonists inhibited growth small and non-small cell lung cancer (see, Moody, T. W. et al., *Proc. Natl, Acad. Sci. USA* 90:4345–9 (1993), Moody, T. W. et al., *Biomedical Res.* 1192, 13 (Suppl. 2) 131).

Gozes, et al. have developed a VIP antagonist that has proven useful for altering the function of the vasoactive intestinal peptide. (See, U.S. Pat. No. 5,217,953 issued to Gozes, et al. (1993)). This VIP antagonist was designed to retain the binding properties of VIP for its receptor, but to lack the amino acid sequence necessary for biological activity. It is believed that biological activity requires, among other factors, a phenylalanine residue at position 6. Amino acids 1–6 of native VIP were therefore replaced by a segment of neurotensin in order to alter the biological activity of native VIP and to change the membrane permeability of the peptide. Three of the six amino acids added in the neurotensin segment are basic. This is in contrast to native VIP which contains no basic residues and only one acidic residue in this region. Indeed, the concept that a tetrapeptide with basic amino acids at both ends and a proline residue adjacent to the N-terminal amino acid is essential for high activity on membrane permeability, has been proven correct for neurotensin and other peptides. As such, the VIP antagonist developed by Gozes, et al. is a hybrid molecule containing an amino acid sequence necessary for VIP receptor binding (i.e., amino acids 7–28 of VIP), and an N-terminal amino acid sequence corresponding to a portion of neurotensin.

Studies have shown that this VIP antagonist effectively antagonizes VIP-associated activity. It has been reported that this VIP antagonist inhibits the growth of VIP receptor bearing tumor cells such as, for example, lung tumor cells (i.e., NSCLC cells). (See, U.S. Pat. No. 5,217,953.)

U.S. Pat. No. 5,565,424, which issued to Gozes, et al. on Oct. 15, 1996, discloses another family of polypeptides which are antagonists of the vasoactive intestinal polypeptide. The VIP antagonists disclosed therein are 10–1000 times more efficacious, i.e., more potent in inhibiting VIP-associated activity than previous VIP antagonists. These superactive VIP antagonists were shown to inhibit cancer growth in lung and glioblastoma cells. Examples of superactive VIP antagonists include amino acid sequences referred to as the "NL-hybrid VIP antagonist", the "S-NL-hybrid VIP antagonist" and the "S-hybrid VIP antagonist".

Although the foregoing VIP antagonist and superactive VIP antagonists have been invaluable, there still remains a need in the art for an even more effective cancer treatment. In addition, a treatment is needed which is effective over a broader range of cancers, for solid tumors, and for more advance stages of cancer. The present invention fulfills these and other needs.

SUMMARY OF THE INVENTION

The present invention relates to a pharmaceutical composition comprising a vasoactive intestinal polypeptide (VIP) antagonist, a chemotherapeutic agent and a pharmaceutically acceptable carrier. The vasoactive intestinal polypeptide antagonists of the present invention comprise the following amino acid sequence:

$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$.

In the above formula, $R^1$ and $R^2$ are independently selected and are functional groups including, but not limited to, the following: hydrogen, $C_1$ to $C_{20}$ alkyls and $C_1$ to $C_{20}$ acyls, provided that at least one of $R^1$ or $R^2$ is hydrogen. $X^1$ and $X^2$, in the above formula, are independently selected from the group consisting of naturally occurring amino acids and amino acid analogs or mimetics, provided that $X^1$ is not methionine (SEQ ID NO:1).

Within the scope of the above formula, certain vasoactive intestinal polypeptide antagonists are preferred, namely those in which $R^1$ is H; $R^2$ is H; $X^1$ is a norleucine residue; and $X^2$ is a valine residue (hereinafter referred to as the "NL-hybrid VIP antagonist") (SEQ ID NO:2). Equally preferred are VIP antagonists in which $R^1$ is $CH_3(CH_2)_{16}CO$—; $R^2$ is H; $X^1$ is a norleucine residue; and $X^2$ is a valine residue (hereinafter referred to as the "S-NL-hybrid VIP antagonist") (SEQ ID NO:3). Also equally preferred are VIP antagonists in which $R^1$ is $CH_3(CH_2)_{16}CO$—; $R^2$ is H; $X^1$ is a methionine residue; and $X^2$ is a valine residue (hereinafter referred to as the "S-hybrid VIP antagonist") (SEQ ID NO:4). Further equally preferred are VIP antagonists in which $R^1$ is a $C_1$ to $C_{20}$ alkyl; $R^2$ is H; $X^1$ is a norleucine residue; and $X^2$ is a valine residue (SEQ ID NO:5). In addition, other preferred VIP antagonists are those in which $X^1$ and $X^2$ are amino acids and amino acid analogs or mimetics of hydrophobic character.

It should be noted, however, that $R^1$, $R^2$, $X^1$ and $X^2$ are selected such that the VIP antagonists of the present invention have other than the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6).

The pharmaceutical compositions of the present invention also comprise a chemotherapeutic agent. In certain aspects, the chemotherapeutic agents of the present invention include, but are not limited to, platinum coordination compounds, topoisomerase inhibitors, antibiotics, antimitotic alkaloids and difluoronucleosides.

In other aspects, the present invention relates to a method of inhibiting the growth of a tumor cell, the method comprising: contacting the tumor cell with an effective amount of the combination of a chemotherapeutic agent and a vasoactive intestinal polypeptide (VIP) antagonist, the VIP antagonist comprising the following amino acid sequence:

$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$ wherein $R^1$, $R^2$, $X^1$ and $X^2$ have been defined above (SEQ ID NOS:1–5), with the proviso that the VIP antagonist does not have the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6).

In this method, suitable chemotherapeutic agents include, but are not limited to, platinum coordination compounds, topoisomerase inhibitors, antibiotics, antimitotic alkaloids and difluoronucleosides. The method includes the combination of VIP antagonist with the chemotherapeutic agent delivered in a simultaneous manner, in combination therapy wherein the VIP antagonist is administered first, followed by the chemotherapeutic agent, as well as the chemotherapeutic agent being delivered first followed by the VIP antagonist. The present invention includes all such methods of administering and contacting tumor cells.

In further aspects, the present invention relates to a method of inhibiting the growth of a tumor cell in a mammalian subject, the method comprising:

administering to the subject an effective amount of the combination of a chemotherapeutic agent and a vasoactive intestinal polypeptide (VIP) antagonist, the VIP antagonist comprising the following amino acid sequence:

$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$ wherein $R^1$, $R^2$, $X^1$ and $X^2$ have been defined above (SEQ ID NOS:1–5), with the proviso that the VIP antagonist does not have the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6).

In this aspect, suitable chemotherapeutic agents include, but are not limited to, platinum coordination compounds, topoisomerase inhibitors, antibiotics, antimitotic alkaloids and difluoronucleosides.

In another embodiment, the present invention provides the use for the manufacture of a medicament for the treatment of inhibiting the growth of tumor cells and or cancer therapy. These and other aspects of the present invention will be described in detail hereinbelow.

DEFINITIONS

The term "independently selected" is used herein to indicate that in a Markush group, for example, $R^1$ and $R^2$ can be identical or different (e.g., $R^1$ and $R^2$ can both be hydrogens, or $R^1$ can be hydrogen and $R^2$ can be $C_{20}$ alkyl, etc.).

The term "contacting" is used herein interchangeably with the following: combined with, added to, mixed with, passed over, incubated with, flowed over, etc. Moreover, the compositions of present invention can be "administered" by any conventional methods such as, for example, parenteral, oral, topical and inhalation routes as described herein.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts include, for example, alkali metal salts, such as sodium and potassium, alkaline earth salts and ammonium salts; The chemotherapeutic agents of the present invention can exist as their pharmaceutically acceptable salts.

"A combination amount sufficient," "an effective combination amount" "therapeutically effective combination amount" or "an effective amount of the combination of" all refer to a combined amount of both the VIP antagonist and the chemotherapeutic agent that is effective to depress, suppress or regress malignant cell growth or that results in amelioration of symptoms associated with cancerous diseases. As used herein, the term "combination" of VIP antagonist with chemotherapeutic agent means the two compounds can be delivered in a simultaneous manner, in combination therapy wherein the VIP antagonist is administered first, followed by the chemotherapeutic agent, as well as wherein the chemotherapeutic agent is delivered first followed by the VIP antagonist. The desired result can be either a subjective relief of a symptom(s) or an objectively identifiable improvement in the recipient of the dosage, a decrease in tumor size, or a decrease in the rate of growth of cancer cells as noted by the clinician or other qualified observer.

The term "synergistic effective amount" refers to a combined amount of both the VIP antagonist and the chemotherapeutic agent that is effective to cause a synergistic effect. Synergy is a chemical phenomenon in which the effectiveness of two active components in a mixture is more than additive, i.e., the effectiveness is greater than the equivalent concentration of either component alone. The effectiveness of the combination therapy of a VIP antagonist and the chemotherapeutic agent is synergistic. Thus, synergism is a result, or function, that is more than the sum of the results, or functions of individual elements.

The terms "treating cancer," "therapy," and the like refer generally to any improvement in the mammal having the cancer, wherein the improvement can be ascribed to treatment with the compositions of the present invention. The improvement can be either subjective or objective. For example, if the mammal is human, the patient may note improved vigor or vitality or decreased pain as subjective symptoms of improvement or response to therapy. Alternatively, the clinician may notice a decrease in tumor size or tumor burden based on physical exam, laboratory parameters, tumor markers or radiographic findings. Some laboratory signs that the clinician may observe for response to therapy include normalization of tests, such as white blood cell count, red blood cell count, platelet count, erythrocyte sedimentation rate, and various enzyme levels. Additionally, the clinician may observe a decrease in a detectable tumor marker. Alternatively, other tests can be used to evaluate objective improvement, such as sonograms, nuclear magnetic resonance testing and positron emissions testing.

"Inhibiting the growth of tumor cells" can be evaluated by any accepted method of measuring whether growth of the tumor cells has been slowed or diminished. This includes direct observation and indirect evaluation, such as subjective symptoms or objective signs as discussed above.

The term "amino acid" refers to naturally occurring and synthetic amino acids as well as amino acid analogs and amino acid mimetics that function in a manner similar to the naturally occurring amino acid. Naturally occurring amino acids are those encoded by the genetic code, as well as those amino acids that are later modified, e.g., hydroxyproline, α-carboxyglutamate and O-phosphoserine. Amino acids analogs refer to compounds that have the same basic chemical structure as a naturally occurring amino acid i.e., an α-carbon that is bound to a hydrogen, a carboxyl group, an amino group and an R-group, e.g. homoserine, norleucine, methionine sulfoxide and methionine methyl sulfonium. Such analogs have modified R groups (e.g. norleucine) or modified peptide backbones, but retain the same basic chemical structure as a naturally occurring amino acid. Amino acid memetics refer to chemical compounds that have a structure that is different from the general chemical structure of an amino acid but that functions in a manner similar to an naturally occurring amino acid.

Some of the amino acids referred to herein are described by shorthand designations as follows:

TABLE I

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser |  |
| Threonine | Thr | T |
| Tryptophan | Trp | W |
| Tyrosine | Tyr | Y |
| Valine | Val |  |

DETAILED DESCRIPTION OF THE INVENTION AND PREFERRED EMBODIMENTS

I. Pharmaceutical Compositions

Figure 1:
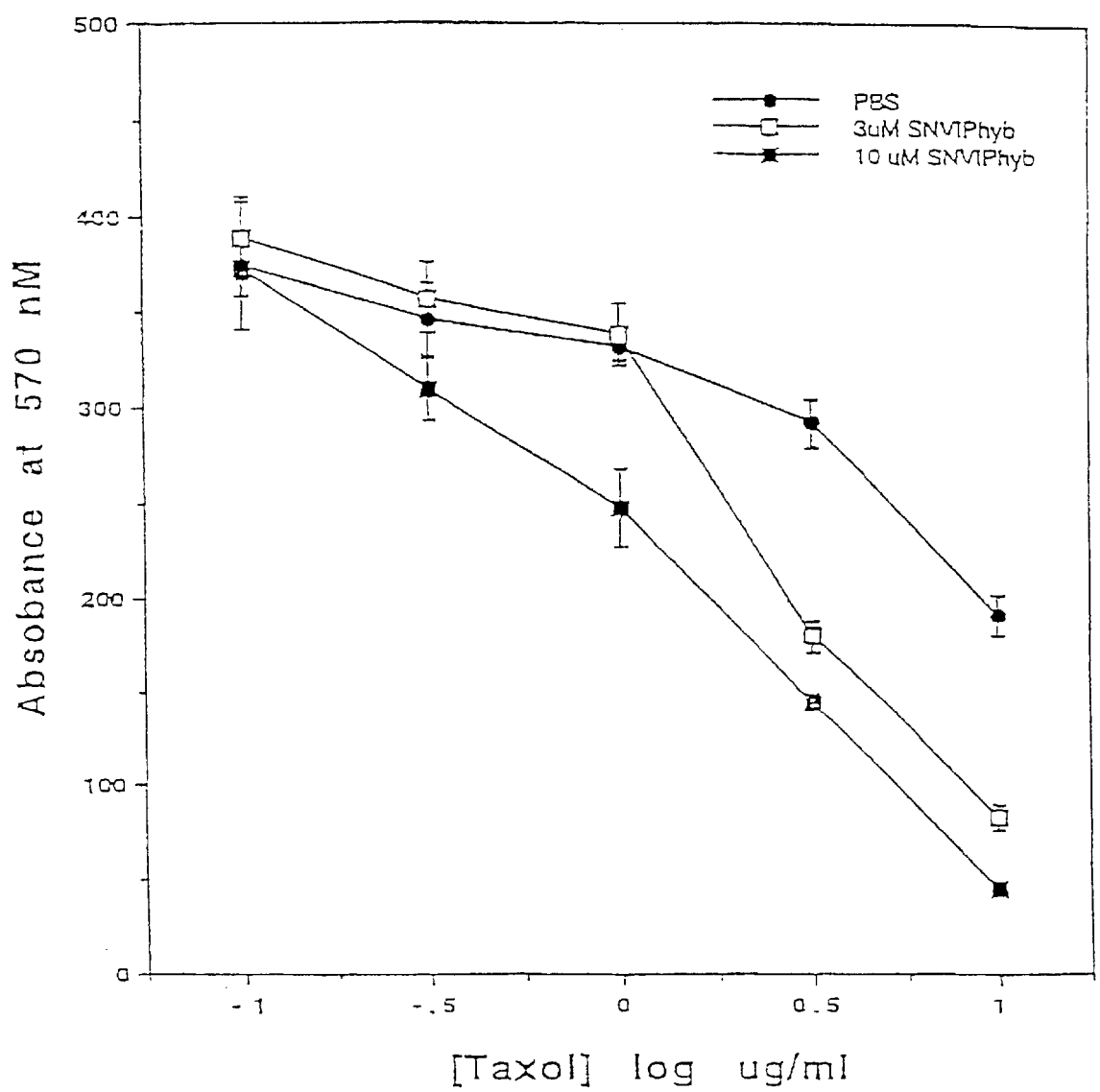
FIG. 1 illustrates a dose response curve in MCF-7 cells using combination therapy of varying concentration of Taxol and SNVIPhyb in a MTT assay.

In one aspect, the present invention provides a pharmaceutical composition comprising a vasoactive intestinal polypeptide (VIP) antagonist, a chemotherapeutic agent and a pharmaceutically acceptable carrier. Surprisingly, the compositions of the present invention achieve synergistic results, i.e., are synergistic. This is a chemical phenomenon in which the effectiveness of the two active components, such as in a mixture, i.e., the VIP antagonist and the chemotherapeutic agent, is more than additive, i.e., is greater than the equivalent concentration of either component alone.

The antagonists comprise the following amino acid sequence:

$R^1$ -Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$.

In the above formula, $R^1$ and $R^2$ are independently selected and may be functional groups including, but not limited to, the following: hydrogen, $C_1$ to $C_{20}$ alkyls and $C_1$ to $C_{20}$ acyls, provided that at least one of $R^1$ or $R^2$ is hydrogen (SEQ ID NO:1). The term "independently selected" is used herein to indicate that the two R groups, $R^1$ and $R^2$, can be identical or different (e.g., both $R^1$ and $R^2$ can be hydrogen or, $R^1$ can be a $C_{16}$ acyl radical and $R^2$ can be hydrogen, etc.). The term "alkyl" is used herein to refer to substituents that are monovalent aliphatic hydrocarbon radicals. The alkyl groups can be straight-chain or branched-chain, with straight-chain alkyl groups (i.e., $C_1$ to $C_{20}$) being preferred. Examples of suitable alkyl radicals include, but are not limited to, the following: methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and icosyl.

The term "acyl" is used herein to refer to an organic radical derived from an organic acid by removal of the hydroxyl group. For example, the acyl radical or group "butyryl" is derived from butanoic acid by removal of the hydroxyl group. Similarly, the acyl group "stearyl" is derived from stearic acid by removal of the hydroxyl group. In accordance with the present invention, the acyl group can be saturated or unsaturated, with acyl groups having from one to twenty carbon atoms (i.e., $C_1$ to $C_{20}$) being preferred. A "saturated" acyl group is one which has no double or triple bonds, whereas an "unsaturated" acyl group is one which has double or triple bonds. Suitable acyl groups include, but are not limited to, the following: butyryl, hexanoyl, octanoyl, lauryl, myristyl, palmityl, stearyl, aracidyl, linoceryl, etc. In addition to the foregoing, it will be readily apparent to those of ordinary skill in the art that a large number of other acyl groups can be derived from various organic acids by removal of the hydroxyl group.

$X^1$ and $X^2$, in the above formula, are independently selected from the group consisting of naturally occurring amino acids, amino acid analogs or amino acid mimetics, provided that $X^1$ is not methionine. The term "independently selected" is used herein to indicate that the two X groups, $X^1$ and $X^2$, may be identical or different (e.g., both $X^1$ and $X^2$ may be valine, etc.). $X^1$ and $X^2$, as previously mentioned, represent a naturally occurring amino acid, an amino acid analog, or amino acid mimetic or a molecule that functions in a manner similar to an amino acid. Suitable amino acids that can be used to form the antagonists of the present invention include, but are not limited to, those listed in Table I.

Within the scope of the above formula, certain vasoactive intestinal polypeptide antagonists are preferred, namely those in which $R^1$ is H; $R^2$ is H; $X^1$ is a norleucine residue; and $X^2$ is a valine residue (SEQ ID NO:2). Equally preferred are VIP antagonists in which $R^1$ is $CH_3(CH_2)_{16}CO$—; $R^2$ is H; $X^1$ is a norleucine residue; and $X^2$ is a valine residue (SEQ ID NO:3). Also equally preferred are VIP antagonists in which $R^1$ is $CH_3(CH_2)_{16}CO$—; $R^2$ is H; $X^1$ is a methionine residue; and $X^2$ is a valine residue (SEQ ID NO:4). Further equally preferred are VIP antagonists in which $R^1$ is a $C_1$ to $C_{20}$ alkyl; $R^2$ is H; $X^1$ is a norleucine residue; and $X^2$ is a valine residue (SEQ ID NO:5). In addition, other preferred VIP antagonists are those in which $X^1$ and $X^2$ are amino acids, amino acid analogs or amino acid mimetics of hydrophobic character. Such amino acids include, but are not limited to, leucine, norleucine, phenylalanine and valine (e.g., $X^1$ is leucine, valine or phenylalanine, and $X^2$ is leucine, norleucine or phenylalanine; SEQ ID NO:8).

It should be noted, however, that $R^1$, $R^2$, $X^1$ and $X^2$ are selected such that the VIP antagonists of the present invention have other than the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6).

In addition, it will be readily apparent to those of ordinary skill in the art that the VIP antagonists of the present invention can be subject to various changes, such as insertions, deletions and substitutions, either conservative or non-conservative, where such changes might provide for certain advantages in their use, i.e., to increase biological activity. By conservative substitutions is meant replacing an amino acid residue with another which is biologically and/or chemically similar, e.g., one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Residues which can be modified without loosing the biological activity of the VIP antagonist can be identified by single amino acid substitutions, deletions, or insertions using conventional techniques known to those of ordinary skill in the art, this is especially true of the VIP antagonists of the present invention being that they are relatively short in length. In addition, the contributions made by the side chains of the residues can be probed via a systematic scan with a specified amino acid (e.g., Ala).

The VIP antagonists of the present invention are relatively short in length and are typically no more than 28 amino acids in length. As such, it is feasible to prepare such VIP antagonists using any of a number of chemical peptide synthesis techniques well known to those of ordinary skill in the art including both solution methods and solid phase methods, with solid phase synthesis being preferred. (see, U.S. Pat. No. 5,565,424, which issued to Gozes, et al. on Oct. 15, 1996).

Solid phase synthesis is started from the carboxy-terminal end (i.e., the C-terminus) of the peptide by coupling a protected amino acid via its carboxyl group to a suitable solid support. The solid support used is not a critical feature of the present invention provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for use as solid supports are well known to those of skill in the art and include, but are not limited to, the following: halomethyl resins, such as chloromethyl resin or bromomethyl resin, hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known to those of ordinary skill in the art.

The acid form of the peptides of the present invention may be prepared by the solid phase peptide synthesis procedure using a benzyl ester resin as a solid support. The corresponding amides may be produced by using benzhydrylamine or methylbenz-hydrylamine resin as the solid support. Those skilled in the art will recognize that when the BHA or MBHA resin is used, treatment with anhydrous hydrofluoric acid to cleave the polypeptide from the solid support produces a polypeptide having a terminal amide group.

The α-amino group of each amino acid used in the synthesis should be protected during the coupling reaction to prevent side reactions involving the reactive α-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the polypeptide synthesis. Protecting groups are well known to those of skill in the art. See, for example, *The Peptides: Analysis, Synthesis, Biology*, Vol. 3: *Protection of functional Groups in Peptide Synthesis* (Gross and Meienhofer (eds.), Academic Press, N.Y. (1981)), the teachings of which are incorporated herein by reference.

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side chain protecting groups must be chosen to render the side chain functional group inert during the synthesis, must be stable under the conditions used to remove the α-amino protecting group, and must be removable after completion of the polypeptide synthesis under conditions that will not alter the structure of the polypeptide.

Illustrative examples of protecting groups for an α-amino group include, but are not limited to, the following: aromatic urethane-type groups such as, for example, fluorenylmethyloxycarbonyl (Fmoc), carbobenzoxy (Cbz), and substituted benzyloxycarbonyls including p-chlorobenzyloxycarbonyl, o-chlorobenzyloxycarbonyl, 2,4-dichlorobenzyloxycarbonyl, 2,6-dichlorobenzyloxycarbonyl, etc., aliphatic urethane-type groups such as, for example, butyloxycarbonyl (Boc), t-amyloxycarbonyl, isopropyloxycarbonyl, 2-(p-biphenylyl)-isopropyloxycarbonyl, allyloxycarbonyl, etc.; and cycloalkyl urethane-type groups such as, for example, cyclopentyloxycarbonyl, cyclohexyloxycarbonyl, cycloheptyloxy-carbonyl, adamantyloxycarbonyl (Adoc), etc. In a presently preferred embodiment, fluorenylmethyloxycarbonyl (Fmoc) is the α-amino protecting group used.

For the side chain amino group present in lysine (Lys), any of the protecting groups described above for the protection of the α-amino group are suitable. Moreover, other suitable protecting groups include, but are not limited to, the following:

butyloxycarbonyl (Boc), p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, t-butyloxycarbonyl, isopropyloxycarbonyl, t-amyloxycarbonyl, cyclopentyloxycarbonyl, cyclohexyl-oxycarbonyl, cycloheptyloxycarbonyl, adamantyloxycarbonyl, p-toluenesulfonyl, etc. In a presently preferred embodiment, the side chain amino protecting group for Lys is butyloxycarbonyl (Boc).

For protection of the guanidino group of arginine (Arg), examples of suitable protecting groups include, but are not limited to, the following: nitro, tosyl (Tos), carbobenzoxy (Cbz), adamantyloxycarbonyl (Adoc), butyloxycarbonyl (Boc), 4-methoxy-2,3,6-trimethylbenzenesulfonyl (Mtr) and 2,2,5,7,8-pentamethylchloroman-6-sulfonyl (PMC). In a presently preferred embodiment, 4-methoxy-2,3,6-trimethyl-benzenesulfonyl and 2,2,5,7,8-pentamethylchloroman-6-sulfonyl are the protecting group used for Arg.

The hydroxyl group on the side chains of serine (Ser), threonine (Thr) or tyrosine (Tyr) can be protected by a $C_1$–$C_4$ alkyl such as, for example, methyl, ethyl and t-butyl, or by a substituted benzyl such as, for example, p-methoxybenzyl, p-nitrobenzyl, p-chlorobenzyl, o-chlorobenzyl and 2,6-dichlorobenzyl. The preferred aliphatic hydroxyl protecting group for Ser, Thr and Tyr is t-butyl.

The carboxyl group of aspartic acid (Asp) may be protected by, for example, esterification using groups such as benzyl, t-butyl, cyclohexyl, cyclopentyl, and the like. For Asp, t-butyl is the presently preferred protecting group. The basic imidazole ring in histidine (His) may be protected by, for example, t-butoxymethyl (Bom), butyloxycarbonyl (Boc) and fluorenylmethyloxycarbonyl (Fmoc). In a preferred embodiment, t-butoxymethyl (Bom) is the protecting group used.

Coupling of the amino acids may be accomplished by a variety of chemistries known to those of skill in the art. Typical approaches involve either the conversion of the amino acid to a derivative that will render the carboxyl group more susceptible to reaction with the free N-terminal amino group of the polypeptide fragment, or use of a suitable coupling agent such as, for example, N,N'-dicyclohexylcarbodimide (DCC) or N,N'-diisopropylcarbodiimide (DIPCDI). Frequently, hydroxybenzotriazole (HOBt) is employed as a catalyst in these coupling reactions. Appropriate synthesis chemistries are disclosed in *The Peptides: Analysis, Structure, Biology*, Vol. 1: *Methods of Peptide Bond Formation* (Gross and Meienhofer (eds.), Academic Press, N.Y. (1979)); and Izumiya, et al., *Synthesis of Peptides* (Maruzen Publishing Co., Ltd., (1975)), both of which are incorporated herein by reference.

Generally, synthesis of the VIP polypeptide is commenced by first coupling the C-terminal amino acid, which is protected at the N-α-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(α-[2,4-dimethoxyphenyl]-Fmoc-amino-methyl)phenoxy resin using N,N'-dicyclohexylcarbodimide (DCC) and hydroxybenzotriazole (HOBt) at about 25 μC for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Nova (Switzerland) or Bachem (Calif.)). Each protected amino acid or amino acid sequence is introduced into the solid phase reactor in excess and the coupling is carried out in a medium of dimethylformamide (DMF), methylene chloride ($CH_2Cl_2$) or, mixtures thereof If coupling is incomplete, the coupling reaction may be repeated before deprotection of the N-α-amino group and addition of the next amino acid. Coupling efficiency may be monitored by a number of means well known to those of skill in the art. A preferred method of monitoring coupling efficiency is by the ninhydrin reaction. Polypeptide synthesis reactions may be performed automatically using a number of commercially available peptide synthesizers (e.go, Biosearch 9500, Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, preferably 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or, by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The polypeptides, i.e., VIP antagonists, of the present invention can be isolated and purified from the reaction mixture by means of peptide purification well known to those of skill in the art, For example, the polypeptides may be purified using known chromatographic procedures such as reverse phase HPLC, gel permeation, ion exchange, size exclusion, affinity, partition, or countercurrent distribution.

B. The Chemotherapeutic Agent

The pharmaceutical compositions of the present invention also include chemotherapeutic agents. Suitable chemotherapeutic agents include, but are not limited to, platinum coordination compounds, topoisomerase inhibitors, antibiotics, antimitotic alkaloids and difluoronucleosides.

In one embodiment of the present invention, the chemotherapeutic agent is a platinum coordination compound. The term "platinum coordination compound" refers to any tumor cell growth inhibiting platinum coordination compound that provides the platinum in the form of an ion. Preferred platinum coordination compounds include, but are not limited to, cis-diamminediaquoplatinum (II)-ion; chloro(diethylenetriamine)-platinum(II)chloride; dichloro(ethylenediamine)-platinum(II), diammine(1,1-cyclobutanedicarboxylato) platinum(II) (carboplatin); spiroplatin; iproplatin; diammine(2-ethylmalonato)-platinum(II); ethylenediaminemalonatoplatinum(II); aqua (1,2-diaminodyclohexane)-sulfatoplatinum(II); (1,2-diaminocyclohexane)malonatoplatinum(II); (4-caroxyphthalato)(1,2-diaminocyclohexane)platinum(II); (1,2-diaminocyclohexane)-(isocitrato)platinum(II); (1,2-diaminocyclohexane)cis(pyruvato)platinum(II); (1,2-diaminocyclohexane)oxalatoplatinum(II); ormaplatin; and tetraplatin.

In certain embodiments, cisplatin is the presently preferred platinum coordination compound employed in the compositions and methods of the present invention. Cisplatin is commercially available under the name PLATINOL™ from Bristol Myers-Squibb Corporation and is available as a powder for constitution with water, sterile saline or other suitable vehicle. Other platinum coordination compounds suitable for use in the present invention are known and are available commercially and/or can be prepared by conventional techniques. Cisplatin, or cis-dichlorodiammineplatinum II, has been used successfully for many years as a chemotherapeutic agent in the treatment of various human solid malignant tumors. More recently, other diamino-platinum complexes have also shown efficacy as chemotherapeutic agents in the treatment of various human solid malignant tumors. Such diamino-platinum complexes include, but are not limited to, spiroplatinum and carboplatinum. Although cisplatin and other diamino-platinum complexes have been widely used as chemotherapeutic agents in humans, they have had to be delivered at high dosage levels that can lead to toxicity problems such as kidney damage.

Advantageously, when cisplatin is used in combination with the VIP antagonists of the present invention, the results obtained are synergistic. That is to say, the effectiveness of the combination therapy of a VIP antagonist and the platinum coordination compound is synergistic, i.e., the effectiveness is greater than the equivalent concentration of either component alone. Therefore, the dosage of the platinum coordination compound can be reduced and thus, the risk of the toxicity problems and other side effects is concomitantly reduced.

In another aspect, the chemotherapeutic agent of the present invention is a topoisomerase inhibitor. Topoisomerases are enzymes that are capable of altering DNA topology in eukaryotic cells. They are critical for cellular functions and cell proliferation. Generally, there are two classes of topoisomerases in eukaryotic cells, type I and type II. Topoisomerase I is a monomeric enzyme of approximately 100,000 molecular weight. The enzyme binds to DNA and introduces a transient single-strand break, unwinds the double helix (or allows it to unwind), and subsequently reseals the break before dissociating from the DNA strand. Various topoisomerase inhibitors have recently shown clinical efficacy in the treatment of humans afflicted with ovarian, cancer, esophageal cancer or non-small cell lung carcinoma.

One especially preferred topoisomerase inhibitor of the present invention is camptothecin and camptothecin analogs. Camptothecin is a water-insoluble, cytotoxic alkaloid produced by *Camptotheca accuminata* trees indigenous to China and *Nothapodytes foetida* trees indigenous to India. Camptothecin exhibits tumor cell growth inhibiting activity against a number of tumor cells. Compounds of the camptothecin analog class are typically specific inhibitors of DNA topoisomerase I. By the term "inhibitor of topoisomerase" is meant any tumor cell growth inhibiting compound that is structurally related to camptothecin. Compounds of the camptothecin analog class include, but are not limited to, topotecan, irinotecan and 9-amino-camptothecin.

In addition to the foregoing topoisomerase inhibitors, such compounds also include, but are not limited to, any tumor cell growth inhibiting camptothecin analog claimed or described in: U.S. Pat. No. 5,004,758, issued on Apr. 2, 1991 and European Patent Application Number 88311366.4, published on Jun. 21, 1989 as Publication Number EP 0 321 122; U.S. Pat. No. 4,604,463, issued on Aug. 5, 1986 and European Patent Application Publication Number EP 0 137 145, published on Apr. 17, 1985, U.S. Pat. No. 4,473,692, issued on Sep. 25, 1984 and European Patent Application Publication Number EP 0 074 256, published on Mar. 16, 1983; U.S. Pat. No. 4,545,880, issued on Oct. 8, 1985 and European Patent Application Publication Number EP 0 074 256, published on Mar. 16, 1983, European Patent Application Publication Number EP 0 088 642, published on Sep. 14, 1983; Wani et al., *J. Med Chem.*, 29, 2358–2363 (1986); Nitta et al., *Proc. 14th International Congr. Chemotherapy*, Kyoto, 1985, Tokyo Press, Anticancer Section 1, p. 28–30, especially a compound called CPT-11. CPT-11 is a camptothecin analog with a 4-(piperidino)-piperidine side chain joined through a carbamate linkage at C-10 of 10-hydroxy-7-ethyl camptothecin. CPT-11 is currently undergoing human clinical trials and is also referred to as irinotecan; Wani et al, *J. Med Chem.*, 23, 554 (1980); Wani et. al., *J. Med Chem*, 30, 1774 (1987); U.S. Pat. No. 4,342,776, issued on Aug. 3, 1982; U.S. patent application Ser. No. 581,916, filed on Sep. 13, 1990 and European Patent Application Publication Number EP 418 099, published on Mar. 20, 1991; U.S. Pat. No. 4,513,138, issued on Apr. 23, 1985 and European Patent Application Publication Number EP 0 074 770, published on Mar. 23, 1983; U.S. Pat. No. 4,399,276, issued on Aug. 16, 1983 and European Patent Application Publication Number 0 056 692, published on Jul. 28, 1982; the entire disclosure of each of which is hereby incorporated by reference. All of the above-listed compounds of the camptothecin analog class are available commercially and/or can be prepared by conventional techniques including those described in the above-listed references. Preferably, the topoisomerase inhibitor is selected from the group consisting of topotecan, irinotecan and 9-aminocamptothecin. Preferably, the topoisomerase inhibitor of the present invention is irinotecan.

Advantageously, when a topoisomerase inhibitor is used in combination with the VIP antagonists of the present invention, the results obtained are synergistic. That is to say, the effectiveness of the combination therapy of a VIP antagonist and the topoisomerase inhibitor is synergistic, i.e., the effectiveness is greater than the equivalent concentration of either component alone. Therefore, the dosage of the topoisomerase inhibitor can be reduced and thus, the risk of the toxicity problems and other side effects is concomitantly reduced.

The preparation of numerous compounds of the camptothecin analog class (including pharmaceutically acceptable salts, hydrates and solvates thereof) as well as the preparation of oral and parenteral pharmaceutical compositions comprising such a compounds of the camptothecin analog class and an inert, pharmaceutically acceptable carrier or diluent, is extensively described in U.S. Pat. No. 5,004,758, issued on Apr. 2, 1991 and European Patent Application Number 88311366.4, published on Jun. 21, 1989 as Publication Number EP 0 321 122, the teachings of which are incorporated herein by reference.

In still yet another embodiment of the present invention, the chemotherapeutic agent is an antibiotic compound. Suitable antibiotic include, but are not limited to, doxorubicin, mitomycin, bleomycin, daunorubicin and streptozocin. The antibiotic doxorubicin is the antibiotic used in a preferred embodiment of the present invention.

Advantageously, when an antibiotic is used in combination with the VIP antagonists of the present invention, the results obtained are synergistic. That is to say, the effectiveness of the combination therapy of a VIP antagonist and the antibiotic compound is synergistic, i.e., the effectiveness is greater than the equivalent concentration of either component alone. Therefore, the dosage of the antibiotic compound can be reduced and thus, the risk of the toxicity problems and other side effects is concomitantly reduced.

In another embodiment, the chemotherapeutic agent is an antimitotic alkaloid. In general, antimitotic alkaloids can be extracted from *Cantharanthus roseus*, and have been shown to be efficacious as anticancer chemotherapy agents. A great number of semi-synthetic derivatives have been studied both chemically and pharmacologically (see, O. Van Tellingen et al, *Anticancer Research*, 12, 1699–1716 (1992)). The antimitotic alkaloids of the present invention include, but are not limited to, vinblastine, vincristine, vindesine, Taxol and vinorelbine. The latter two antimitotic alkaloids are commercially available from Eli Lilly and Company, and Pierre Fabre Laboratories, respectively. (see, U.S. Pat. No. 5,620, 985, issued on Apr. 15, 1997). In a preferred aspect of the present invention, the antimitotic alkaloid is vinorelbine.

Advantageously, when an antimitotic alkaloid is used in combination with the VIP antagonists of the present invention, the results obtained are synergistic. That is to say, the effectiveness of the combination therapy of a VIP antagonist and an antimitotic alkaloids compound is synergistic, i.e., the effectiveness is greater than the equivalent concentration of either component alone. Therefore, the dosage of the antimitotic alkaloid can be reduced and thus, the risk of the toxicity problems and other side effects is concomitantly reduced.

In another embodiment of the present invention, the chemotherapeutic agent is a difluoronucleoside. 2'-deoxy-2',2'-difluoronucleosides are known in the art as having antiviral activity. Such compounds are disclosed and taught in U.S. Pat. Nos. 4,526,988 and 4,808614. European Patent Application Publication 184,365 discloses that these same difluoronucleosides have oncolytic activity. Preferably, the 2'-deoxy-2',2'-difluoronucleoside used in the compositions and methods of the present invention is 2'-deoxy-2',2'-difluorocytidine hydrochloride, also known as gemcitabine hydrochloride. Gemcitabine is commercially available or can be synthesized in a multi-step process as disclosed and taught in U.S. Pat. Nos. 4,526,988, 4,808614 and 5,223,608, the teachings of which are incorporated herein by reference.

Advantageously, when a difluoronucleoside is used in combination with the VIP antagonists of the present invention, the results obtained are synergistic. That is to say, the effectiveness of the combination therapy of a VIP antagonist and a difluoronucleoside compound is synergistic, i.e., the effectiveness is greater than the equivalent concentration of either component alone. Therefore, the dosage of the difluoronucleoside can be reduced and thus, the risk of the toxicity problems and other side effects is concomitantly reduced.

II. Uses, Dosages and Schedules

The compositions of the present invention are useful for treating a wide variety of cancers and cancerous tumors. In a preferred embodiment, the cancerous tissue and tumors contain VIP receptors. Such cancers include, by way of example and not limitation, carcinomas such as pharynx, colon, rectal, pancreatic, stomach, liver, lung, breast, skin, prostate, ovary, cervical, uterine and bladder cancers, leukemias, lymphomas, gliomas, glioblastomas, retinoblastomas, and sarcomas.

As such, in another embodiment, the present invention relates to a method for inhibiting the growth of a tumor cell, the method comprising: contacting the tumor cell with an effective amount of a combination of a chemotherapeutic agent and a vasoactive intestinal polypeptide (VIP) antagonist, the VIP antagonist comprising the following amino acid sequence:

$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$ wherein $R^1$, $R^2$, $X^1$ and $X^2$ have been defined above (SEQ ID NOS:1–5), with the proviso that the VIP antagonist does not have the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6).

As explained herein, suitable chemotherapeutic agents include, but are not limited to, platinum coordination compounds, topoisomerase inhibitors, antibiotics, antimitotic alkaloids and difluoronucleosides.

In another embodiment, the present invention relates to a method of inhibiting the growth of a tumor cell in a mammalian subject, the method comprising: administering to the subject an effective amount of a combination of a chemotherapeutic agent and a vasoactive intestinal polypeptide (VIP) antagonist, the VIP antagonist comprising the following amino acid sequence:

$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$ wherein $R^1$, $R^2$, $X^1$ and $X^2$ have been defined above (SEQ ID NOS:1–5), with the proviso that the VIP antagonist does not have the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6).

wherein $R^1$, $R^2$, $X^1$ and $X^2$ have been defined above, with the proviso that the VIP antagonist does not have the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn.

In this aspect, suitable chemotherapeutic agents include, but are not limited to, platinum coordination compounds, topoisomerase inhibitors, antibiotics, antimitotic alkaloids and difluoronucleosides. Mammalian subjects include, but are not limited to, humans, laboratory animals, domestic pets and farm animals. The methods include the administration of the combination of VIP antagonist with chemotherapeutic agent wherein the two components can be delivered in a simultaneous manner, in combination therapy wherein the VIP antagonist is administered first, followed by the chemotherapeutic agent, as well as wherein the chemotherapeutic agent is delivered first followed by the VIP antagonist.

In accordance with the above methods, tumor cells include, but are not limited to, lung, colon, breast, ovarian, prostate and hepatic tumor cells as well as squamous cell carcinomas. In a presently preferred embodiment, the tumor cells are present in a mammalian subject. In a further preferred embodiment, the above methods further comprises the step of observing for a reduction in the growth of the tumor cells.

Compositions suitable for use in the methods of the present invention can readily be identified using in vitro and in vivo screening assays. Such assays may screen for the ability of a particular composition to inhibit malignant tumor cell growth or to abolish tumorigenicity of malignant cells in vitro or in vivo, For instance, tumor cell lines can be exposed to varying concentrations of a composition of interest, and the viability of the cells can be measured at set time points using the alamar Blue® assay (commercially available from BioSource, International of Camarillo, Calif.). When alamar Blue dye is added to the culture medium, the dye is reduced by cellular mitochondrial enzymes yielding a soluble product with substantially enhanced fluorescence. This fluorescence can be measured with a fluorimeter, whereby the signal is directly proportional to the cell number. Using this information, $IC_{50}$ (concentration of composition lethal to 50% of a cell culture as compared to a control culture) values for the compositions of interest can be readily be calculated. Generally, compositions useful in the methods of the present invention will exhibit an $IC_{50}$ in the range of about 0.1 to 20 $\mu$M, as measured by the assay.

As will be appreciated by the skilled artisan, many varieties of malignant tumor cell cultures and cell lines can be used to screen for activity, including but not limited to, MDA MB 231 (breast), MCF-7 (breast), MDA MB 468 (breast), Siha (squamous cell carcinoma), A549 (non-small cell lung), HL-60 (leukemia) Ovcar-3 (ovarian), etc. Of course, other in vitro and/or in vivo assays to screen for anti-tumor and/or anti-cancer activity known to and used by the skilled artisan can also be employed to identify effective compounds useful in the methods of the present invention.

Treatment of a diverse range of tumors can be obtained using the compositions of this invention. In addition, the compositions and methods of the present invention can be tested against standard NIH-recommended models. See, for example Driscoll, "The Preclinical New Drug Research Program of the National Cancer Institute, *Cancer Treatment Reports*, 68:63–76 (1984). Further in vivo and in vitro models that are routinely employed in National Cancer Institute sponsored drug screening evaluations for identifying utility against human neoplasia can be employed to confirm the utility of the instant invention. (see, M. Boyd, The NCI in vitro Anticancer Drug Discovery Screen, Anticancer Development Guide" (B. Teicher (ed.), 1995, Hummna Press, Totawa, N.J.) In addition, the compositions of the present invention can be screened in the National Cancer Institute panel of 60 human tumor cell lines.

The pharmaceutical compositions of the present invention are suitable for use in a variety of drug delivery systems. Suitable formulations for use in the present invention are found in *Remington's Pharmaceutical Sciences* (Mack Publishing Company, Philadelphia, Pa., 17th ed. (1985)), which is incorporated herein by reference. In addition, for a brief review of methods for drug delivery, see, Langer, *Science* 249:1527–1533 (1990), which is incorporated herein by reference.

The pharmaceutical compositions of the present invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of a VIP antagonist, a chemotherapy agent as described above, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the VIP antagonists and chemotherapeutic agents are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, the VIP antagonists and chemotherapy agents of the present invention are administered to a patient in a combination amount sufficient to inhibit tumor growth. An amount adequate to accomplish this is defined as "therapeutically effective combination dose." The methods include the administration of the combination of VIP antagonist with chemotherapeutic agent wherein the two components are delivered in a simultaneous manner, in combination therapy wherein the VIP antagonist is administered first, followed by the chemotherapeutic agent, as well as wherein the chemotherapeutic agent is delivered first followed by the VIP antagonist.

Effective combination amounts for this use will depend on, for example, the particular chemotherapeutic agent, the VIP antagonist employed, the VIP-associated activity to be inhibited or antagonized (e.g., tumor growth) the manner of administration, the weight and general state of health of the patient, and the judgment of the prescribing physician. For example, for inhibition of tumor growth (e.g., NSLC or neuroblastoma), an amount of VIP antagonist falling within the range of 0.35 $\mu$g to 3.5 $\mu$g per 100 g tumor, injected directly into the solid tumor would be a therapeutically effective combination amount. The amount of chemotherapeutic agent will depend in part to the chemical class. The range of 0.01 $\mu$g to 1 g per 100 g tumor, injected directly into the solid tumor would be a therapeutically effective combination amount.

The term "inhibiting the growth of tumor cells", as used herein, is the inhibition of the growth of tumor cells which are sensitive to the method of the subject invention, i.e., therapy involving the administration of an effective amount of the combination of a VIP antagonist and a chemotherapeutic agent to a human afflicted therewith. Preferably, such treatment also leads to the regression of tumor growth, i.e., the decease in size of a measurable tumor. Most preferably, such treatment leads to the complete regression of the tumor. By the term "administering" or "administered" as used herein is meant parenteral and/or oral administration. By "parenteral" is meant intravenous, subcutaneous and intramuscular administration. In the methods of the present invention, the VIP antagonists can be administered simultaneously with the chemotherapeutic agent, or the VIP antagonists can be administered sequentially, in either order.

It will be appreciated that the actual preferred method and order of administration will vary according to, inter alia, the particular formulation of the VIP antagonist being utilized, the particular formulation of chemotherapeutic agent (such as cisplatin) being utilized, the particular tumor cells being treated, and the particular host being treated. The optimal method and order of the combination therapy for a given set of conditions can be ascertained by those skilled in the art using conventional techniques and in view of the information set out herein.

For instance, it will be appreciated that the actual preferred course of therapy will vary according to, inter alia, the mode of administration of the VIP antagonist, the particular formulation of the chemotherapeutic agent being utilized, the mode of administration of the compounds, the particular tumor cells being treated and the particular host being treated. The optimal course of therapy for a given set of conditions can be ascertained by those skilled in the art using conventional course of therapy determination tests and in view of the information set out herein.

The invention will be described in greater detail by way of specific examples. The following examples are offered for illustrative purposes, and are not intended to limit the invention in any manner.

III. EXAMPLES

Example I

This Example illustrates that a VIP antagonist was able to enhance the antiproliferative activity of various chemotherapeutic agents.

Assays were performed with cell lines derived from colon cancer and prostate cancer. Proliferation was assessed using the MTS colorimetric assay of mitochondrial function for living cells. The VIP antagonist (stearyl-Nle17-neurotensin 6–11 VIP 7–28) was used. This example illustrates that the lipophilic antagonist was able to enhance the antiproliferative activity of various chemotherapeutic agents, i.e., doxorubicine, vinorelbine, gemcitabine; irinotecan, and cisplatin.

The effect was synergistic for doxorubicine; vinorelbine; irinotecan and cisplatin. 2 mM of the antagonist that produced a 15–20% growth inhibition of the nonsmall cell lung cancer line reduced the $IC_{50}$ by 2–4 fold for most of the chemotherapeutic agents tested. Higher antagonist concentrations were even more efficacious, maintaining a synergistic effect. Chemotherapeutic treatment of advanced solid tumors, like nonsmall cell lung cancer, colon cancer or prostate cancer achieves response rate between 10–30% with significant toxicity. Combination of the lipophilic VIP antagonist with the preferred chemotherapeutic agents can greatly enhance the response rate. By permitting a dose reduction, side effects will also be reduce.

Example 2

This example illustrates the effect of SNVIPhyb in inhibiting cancer.

The ability of SNVIPhyb to inhibit cancer growth was investigated. Using a MTT assay, 10 $\mu$M SNVIPhyb had little effect on MCF-7 breast cancer proliferation. The effects of SNVIPhyb were then investigated in the presence of Taxol, which affects microtubules, causing dividing cells to arrest in the mitosis (M) phase of growth. Taxol had little effect on MCF-7 cells at 1 $\mu$g/mL, and half maximally ($IC_{50}$) inhibited growth at 12 $\mu$g/mL. In the presence of 3 $\mu$M SNVIPhyb, the Taxol dose response curve was shifted to the left, and the $IC_{50}$ was 24 $\mu$g/mL. These results indicate that SNVIPhyb increases the cytotoxicity of Taxol using MCF-7 breast cancer cells. Similar results were obtained using doxorubicin.

The effect of SNVIPhyb was investigated on other epithelial cancer cell lines. Table 2 shows that $IC_{50}$ values for Taxol was 8–15 $\mu$g/mL in lung (NCI-H157 and NCI-H1299), breast (MCF-7), pancreatic (CAPAN) and prostate (PC-3) cancer cell lines. In the presence of 10 $\mu$M SNVIPhyb, the $IC_{50}$ values decreased to 2.5–5 $\mu$g/mL. Thus, the potency of Taxol increased 3–6 fold in the presence of SNVIPhyb in epithelial cancer cells. SNVIPhyb may inhibit proliferation at the G1 to S phase, whereas Taxol inhibits proliferation at the M phase. Therefore, SNVIPhyb and Taxol are synergistic at inhibiting cancer cell proliferation. As a result, in the presence of SNVIPhyb, less Taxol is needed to kill cancer cells. FIG. 1 illustrates a dose response curve in MCF-7 cells using combination therapy of varying concentration of Taxol and SNVIPhyb.

TABLE 2

Potency of Taxol on cancer cells.

| Cell line | IC$_{50}$ | IC$_{50}$ with 10 μM SNVIPhyb |
|---|---|---|
| Lung Cancer | | |
| NCI-H157 | 10 | 2.5 |
| NCI-H1299 | 08 | 3.0 |
| Breast cancer | | |
| MCF-7 | 12 | 2.0 |
| Pancreatic cancer | | |
| CAPAN | 10 | 3.0 |
| Prostate Cancer | | |
| PC-3 | 15 | 5.0 |

The mean IC$_{50}$ value (μg/mL) of 8 determinations is indicated.

Example 3

The example illustrates the effects of VIP receptor antagonists on glioblastoma cell lines.

The effects of VIP receptor antagonists on glioblastoma cell lines were investigated. Neurotensin $_{6-11}$ VIP$_{7-28}$ (VIPhybrid), (N-Stearyl-Norleucine$_{17}$) VIPhybrid ((SNVIPhybrid) and PTC4495 inhibited $^{125}$I-VIP binding to U-87 cells with IC$_{50}$ values of 70,500 and 7000 nM, respectively. Using molecular biology techniques, VIP$_1$ receptor mRNA was detected in glioblastoma cells by RT-PCR and Northern blot. (SN)VIPhybrid (1 μM) had no effect on basal cAMP but strongly inhibited the increase in cAMP caused by 10 nM VIP and the order of peptide potency was (SN)VIPhybrid>VIP hybrid >PTC4495. (SN) VIPhybrid was more potent than VIP hybrid at inhibiting U-87 colony formation in vitro using soft agar. Using an MTT assay, 1 μM (SN)VIPhybrid had little effect on basal proliferation but synergistically interacted with Taxol to inhibit growth. These data indicate that VIP receptor antagonists can enhance the potency of chemotherapeutic agents to inhibit glioblastoma proliferation.

Example 4

This example illustrates in vitro interaction between a potent lipophilic VIP antagonist, stearyl-nle-VIP-hybrid (SNH) and chemotherapy.

Materials and Methods

A. Cell Lines

NCI-H727 non-small cell lung cancer (carcinoid)
LNCaP prostate cancer
HT-29 human colon cancer
CT-26 murine colon cancer NCI-H727 and LNCaP were grown in RPMI 1640 medium supplemented with 10% heat inactivated FCS, L-glutamine and antibiotics. HT-29 and CT-26 were grown in DMEM medium supplemented with 10% heat-inactivated FCS (fetal calf serum), L-glutamine and antibiotics. The cells were cultured in 5% $CO_2$/95% air at 37 μC and used during their exponential growth phase. Routinely, the cells which are adherent, were split when a subconfluent monolayer was formed. In different experiments, various concentration of FCS were used.

B. Drugs

Taxol (Mead Johnson), irinotecan-CPT$_{11}$ (Rhone-Poulenc Rorer), doxorubicine (Farmitalia), gemcitabine (Lilly), vinorelbine (Navelbine-Pierre Fabre Medicament), cisplatin (Abic-Israel) and 5-fluorouracil (Abic-Israel) were dissolved initially according to manufacturer's instructions and further diluted in PBS.

C. Peptides

The lipophilic VIP antagonist: SNH was synthesized as previously described (Gozes and Fridkin, 1992). The antagonist was first dissolved in DMSO and further diluted in PBS. The maximum amount of DMSO added to the culture was 0.02%, and has no effect on the proliferation of the cancer cells.

VIP: His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-AsnNH$_2$ (SEQ ID NO:7)

SNH: Stearyl-Lys-Pro-Arg-Arg-Pro-Tyr-Thr-Asp-Asn-Tyr-Thr-Arg-Leu-Arg-Lys-Gln-Nle-Ala-Val-Lys-Lys-Tyr-Leu-Asn-Ser-Ile-Leu-AsnNH$_2$ (SEQ ID NO:3)

D. In vitro Cytotoxicity

For growth inhibition experiments, subconfluent adherent cells were washed with PBS and treated with trypsin/versene. The cells were pelleted and resuspended in medium to a final concentration of 75,000 cells/mL for NCI-H727. 50,000 cells/mL for LNCaP and HT-29 and 25000 cells/mL for CT-26. These different concentrations were used in order to avoid confluence in the wells at the end of the experiment and correspond to the different doubling times of the cell lines.

On day 0, cells suspensions (100 mL) were dispensed using a multi-channel pipet into the individual wells of a 96-well tissue culture plate (Nuncion, Nunc Brand Products). Each plate had a blank column containing medium only and a control column. Cells were incubated for 24 hours in a humidified atmosphere of 95% air/5% $CO_2$ at 37° C. before treatment. On day 1, the cells were treated with different drugs and schedules and maintained under the same conditions.

On day 4, viable cell number was determined by a modified MTT assay i.e., MTS non-radioactive cell proliferation assay (Promega). Briefly, 25 mL of freshly prepared MTS/PMS solution was added to each individual well and after 1–3 hours of incubation (the optimal time was determined for each cell line) absorbance at 490 nm was measured using a multiscan plate reader. Results were finally expressed as percentage of the control, which was obtained from the samples with no drug treatment. Dose-response curves were plotted using a Sigma-Plot software and statistically analyzed using Student test.

E. Inhibition of Cell Growth by SNH

Figure 2:
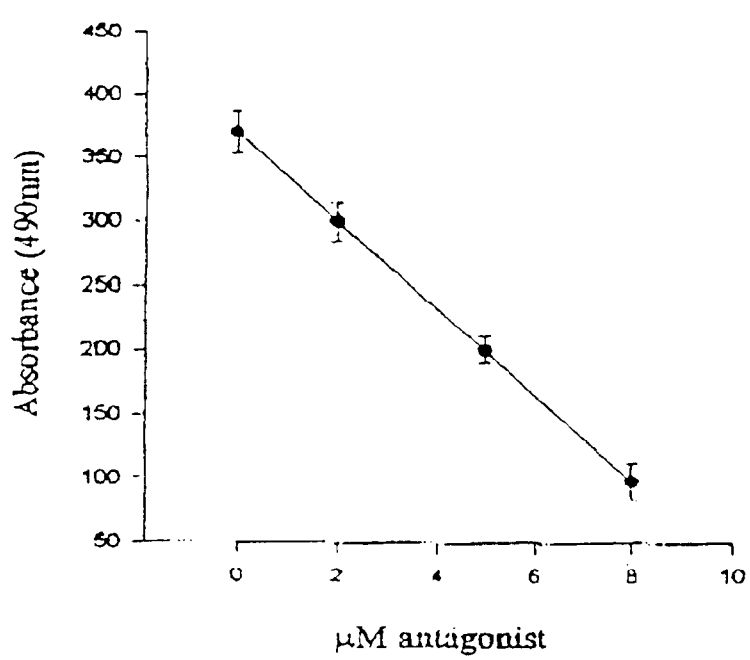
FIG. 2 illustrates a dose response curve of SNH at concentrations ranging from 2 $\mu$M–10 $\mu$M.
Figure 3:
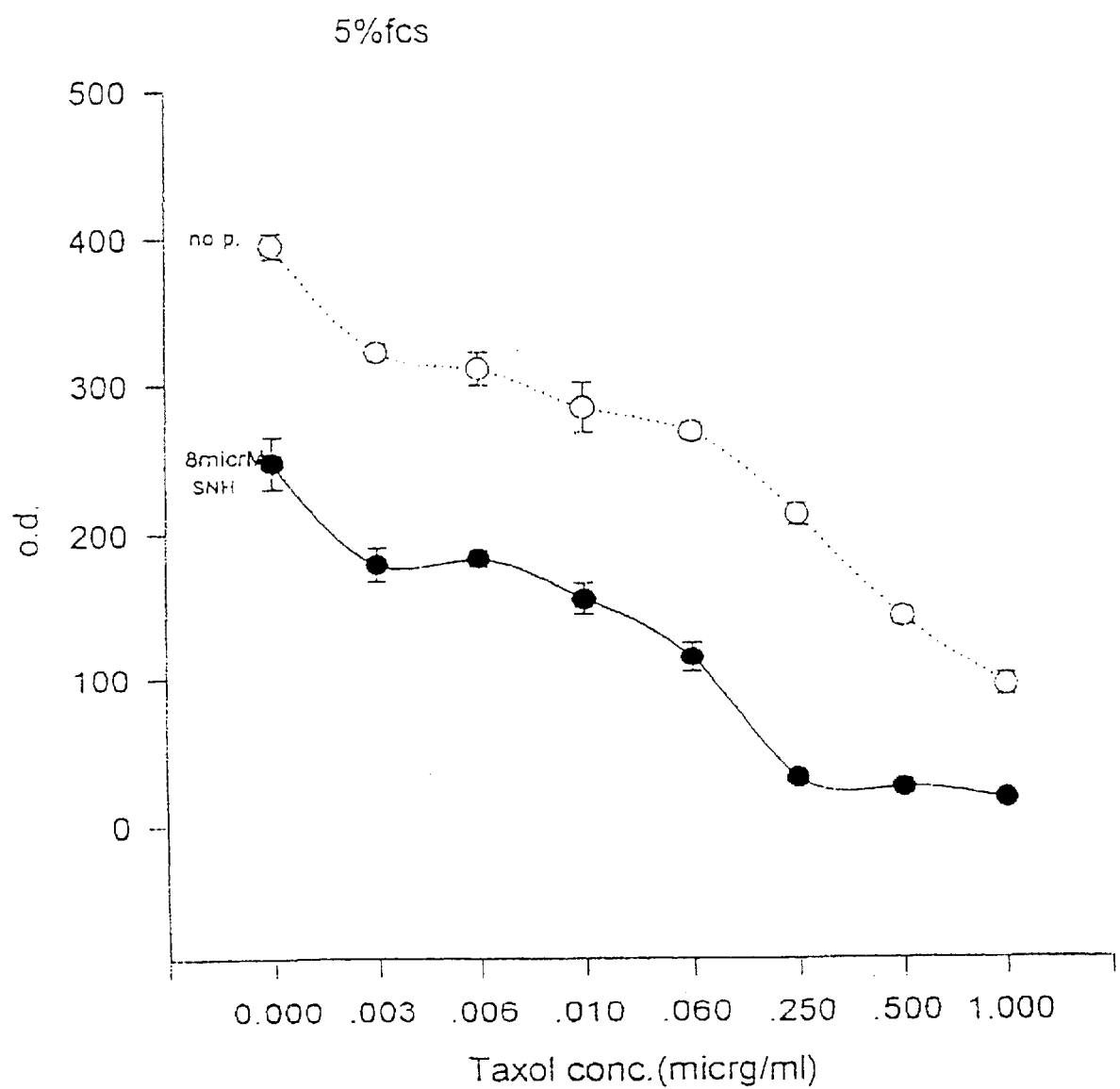
FIG. 3 illustrates a dose response curve in NCI-H727 cell line (non-small cell lung cancer) using the combination therapy of SNH and Taxol.

To determine the effect of the lipophilic VIP antagonist SNH on cell proliferation, cells plated in 96-well microplates for 24 hours as described, were treated with various concentrations of SNH. The peptide was diluted in PBS and 10 mL of the peptide solution was added to each well for a final concentration of the peptide between $10^{-5}10^{-9}$ M. The solvent was added to the control wells. In this assay, 10 mM of SNH significantly inhibits the growth of cancer cells. A dose-response curve was obtained at concentrations ranging from 2 μM–10 μM (see, FIG. 2). The effect is dependent on the FCS concentration, and at concentrations of FCS lower than 2%, an 8–10 mM concentration of SNH produces complete or almost complete death of the cancer cells. Similar results were obtained using one dose of SNH with 24 hour treatment (the medium was exchange 24 hours after the addition of the peptide and the cells incubated for other 48 hours with medium only) and with 72 hours of treatment (no medium exchange). The effects of an 8 hours treatment were slightly less, showing that most of the effect is in the initial hours of exposure and much more dose than time dependent. This can be explained by the fact that even if the lipophilic compound are much more stable, they may still undergo degradation in the presence of FCS. A 6 hour incubation period with 8 μM SNH, followed by a 66 hour fresh-medium period, resulted in a 40% reduction in viable cells (see, FIG. 3). These results suggest that most of the SNH effect is quite rapid.

F. Combined Effects of SNH and Chemotherapeutic Agents

For the experiments with the combinations of VIP antagonists and chemotherapeutic agents, on day 0, the cells were plated for 24 hours in medium supplemented with 5% FCS. On day 1, the peptide was added to the wells followed 1 hour later by the chemotherapeutic agents. In each case, the corresponding volume of the solvent was added to the controls, so that each plate had a blank column containing 1) medium only, 2) a control column containing cells but no drugs, 3) at least triplicates treated with SNH only, 4) chemotherapeutic drugs only and 5) combination of SNH and chemotherapy. The chemotherapeutic drugs were tested over 7 concentrations, covering as much as possible of the dose response curve of each individual drug. 24 hours later, the medium was exchanged and the cells incubated under the same conditions for another 48 hours. On day 4 the number of viable cells was determined by MTS assay. Using a shorter treatment, consisting of 4 hours of exposure to peptide followed by 4 hours exposure to chemotherapy, similar results were obtained.

Figure 4:
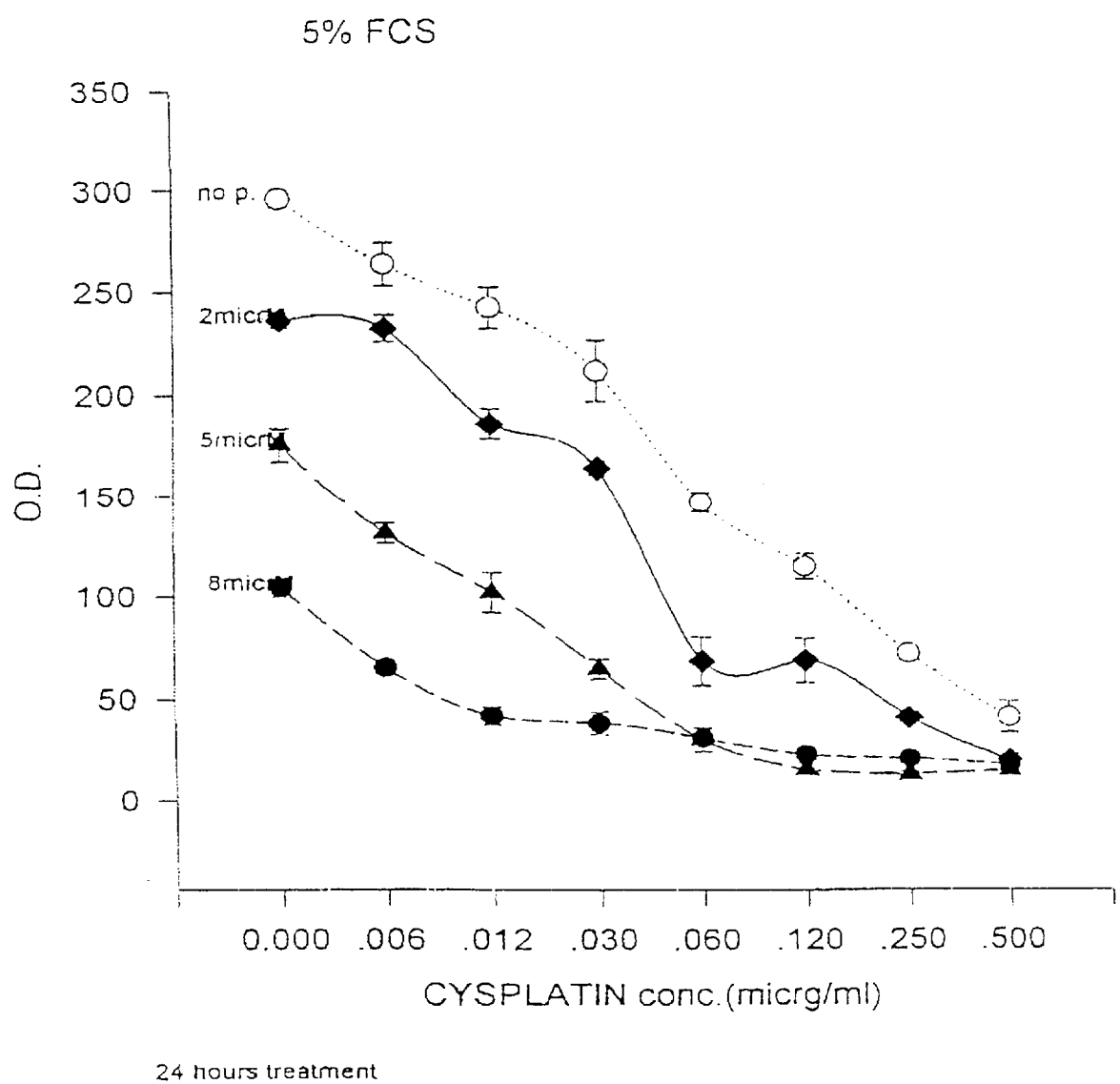
FIG. 4 illustrates a dose response curve in NCI-H727 cell line (non-small cell lung cancer) using the combination therapy of SNH and cisplatin.
Figure 5:
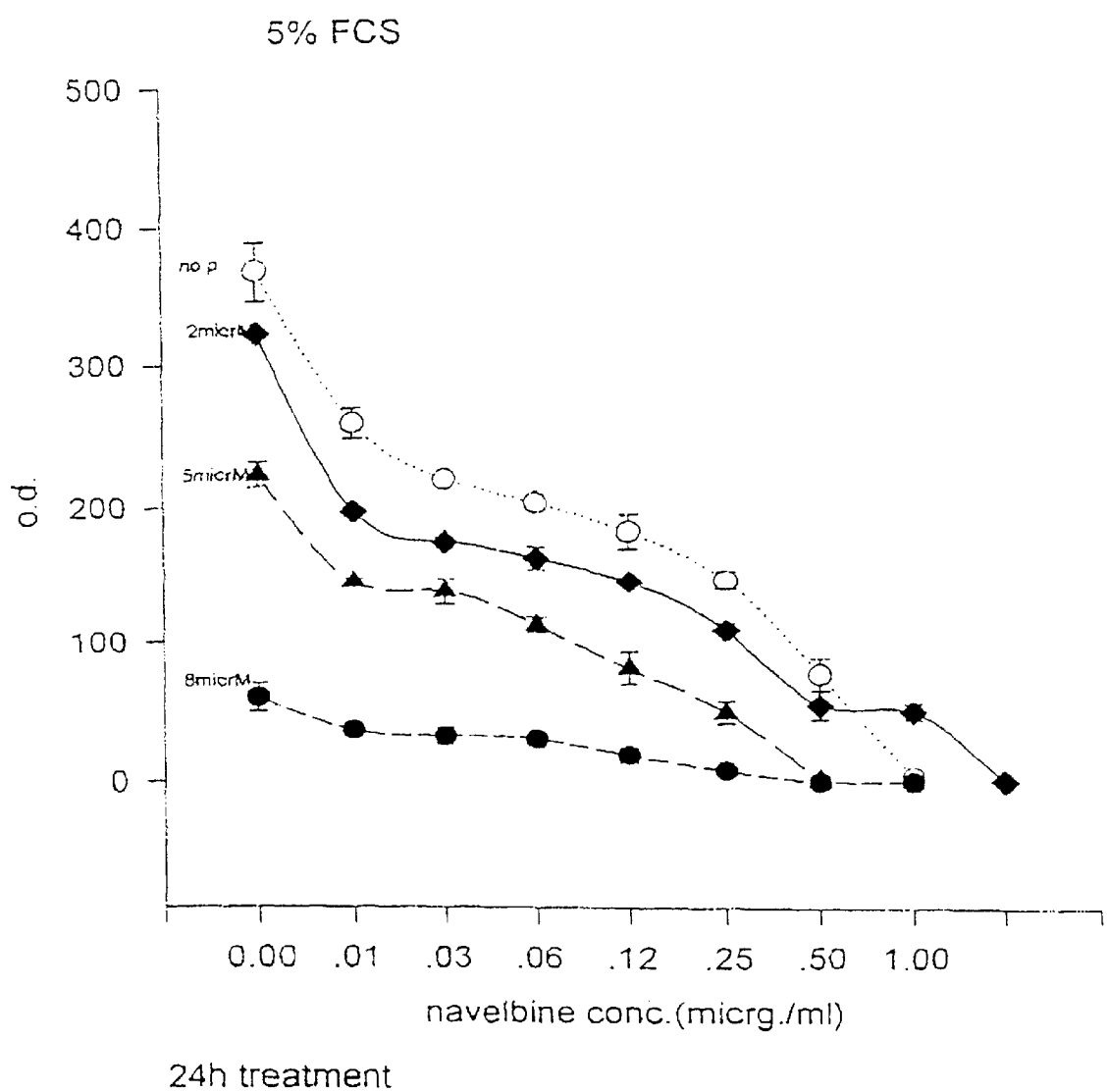
FIG. 5 illustrates a dose response curve in NCI-H727 cell line (non-small cell lung cancer) using the combination therapy of SNH and navelbine.
Figure 6:
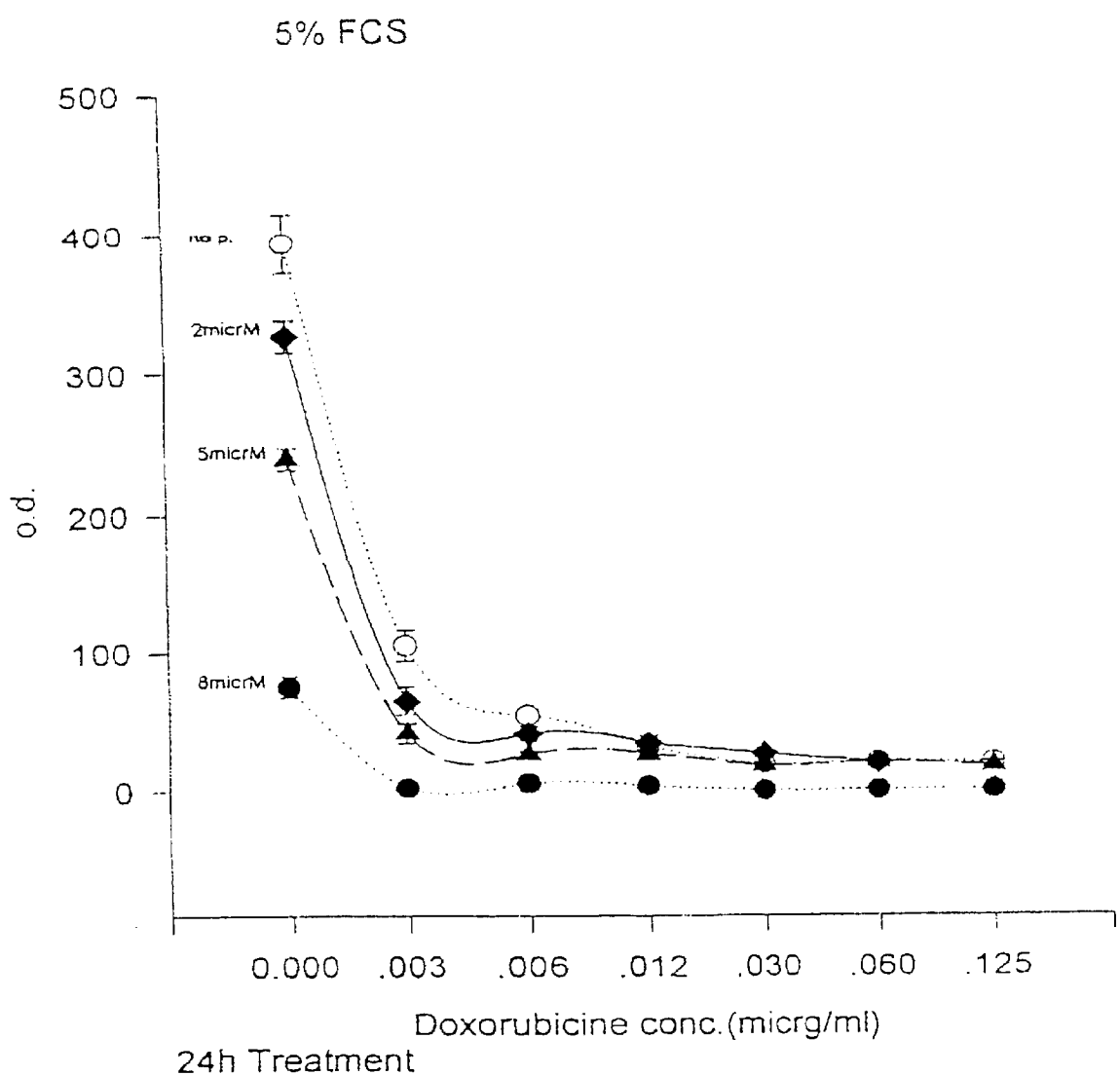
FIG. 6 illustrates a dose response curve in NCI-H727 cell line (non-small cell lung cancer) using the combination therapy of SNH and doxorubicine.
Figure 7:
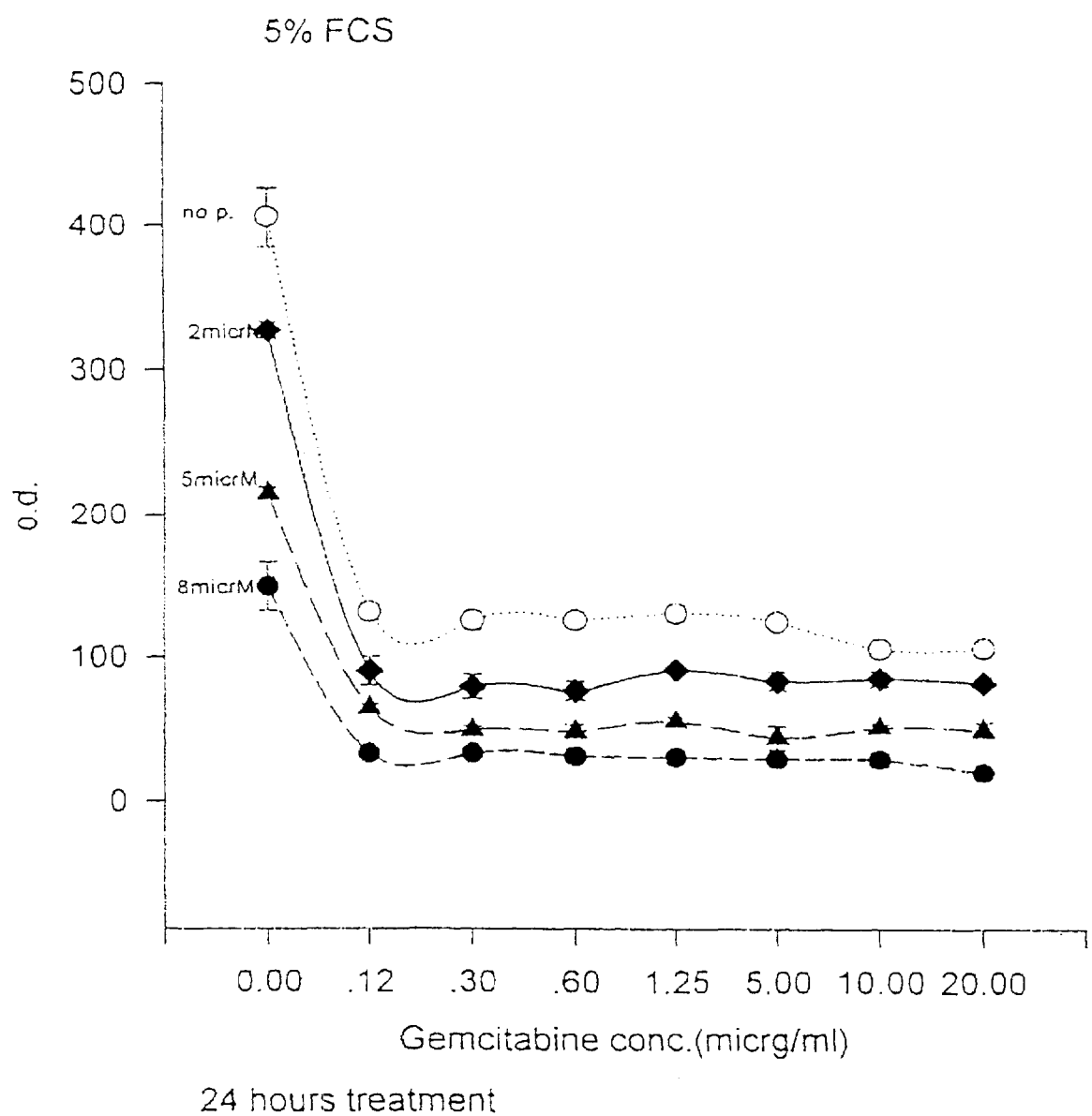
FIG. 7 illustrates a dose response curve in NCI-H727 cell line (non-small cell lung cancer) using the combination therapy of SNH and gemcitabine.
Figure 8:
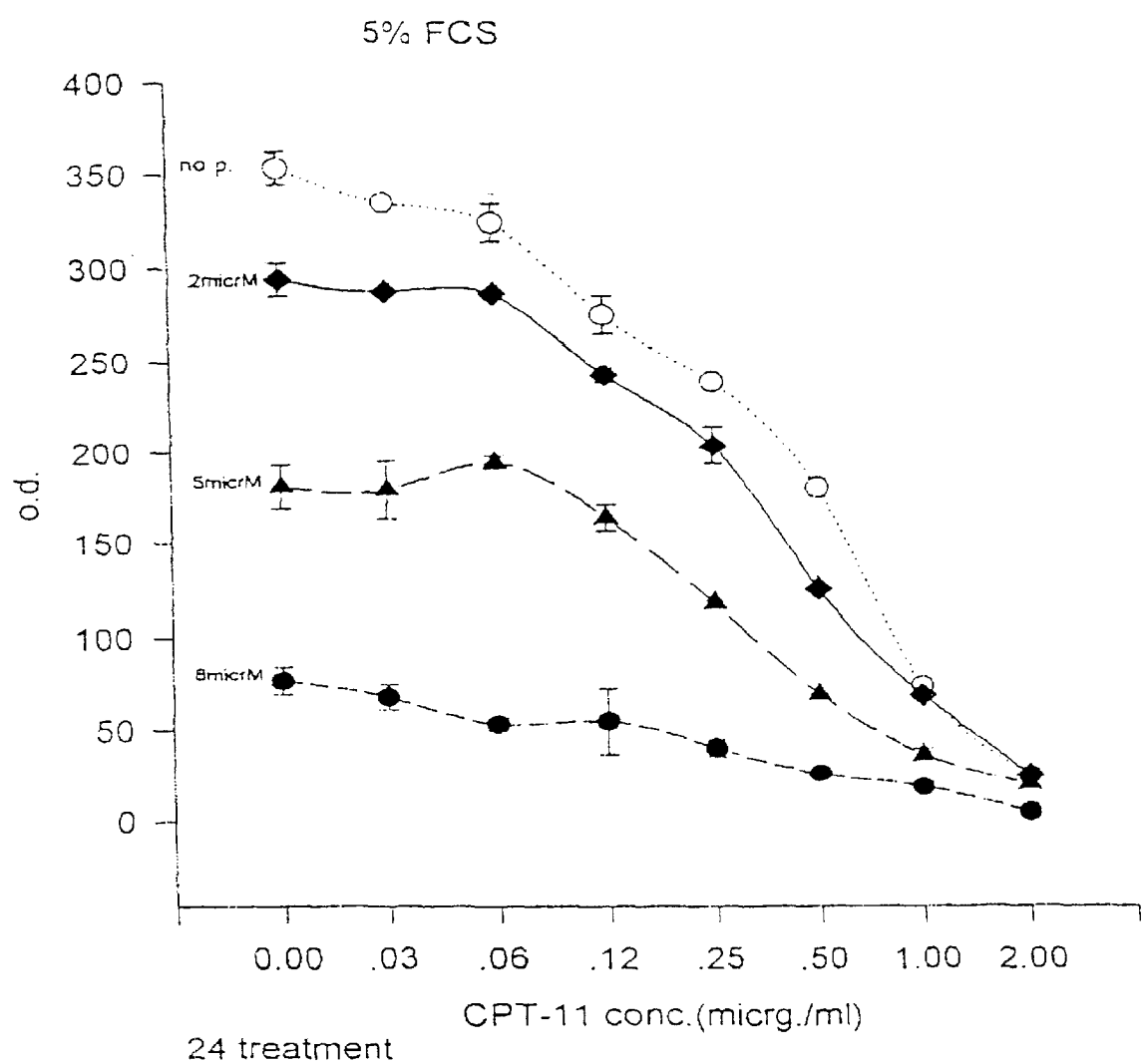
FIG. 8 illustrates a dose response curve in NCI-H727 cell line (non-small cell lung cancer) using the combination therapy of SNH and CPT-11.
Figure 9:
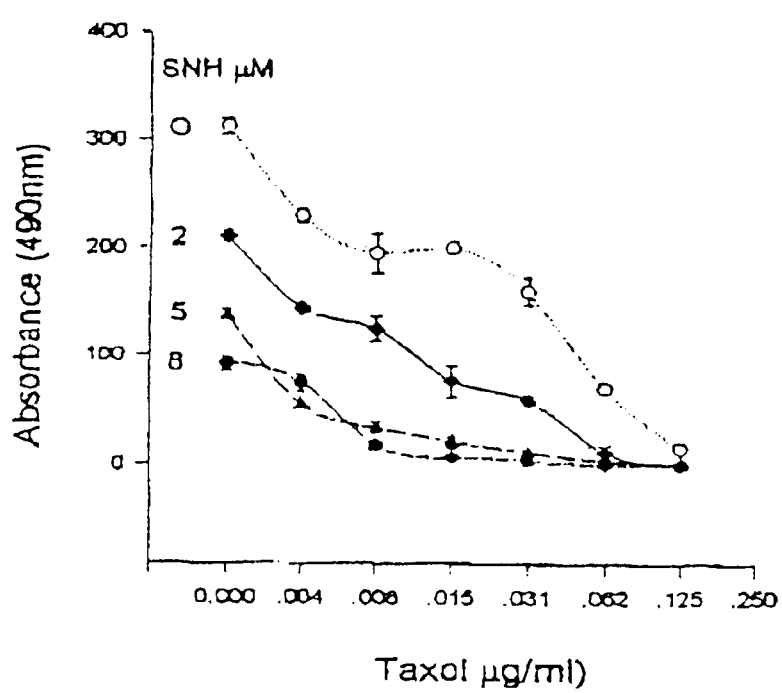
FIG. 9 illustrates a dose response curve using combination therapy of varying concentration of Taxol and SNH.
Figure 10:
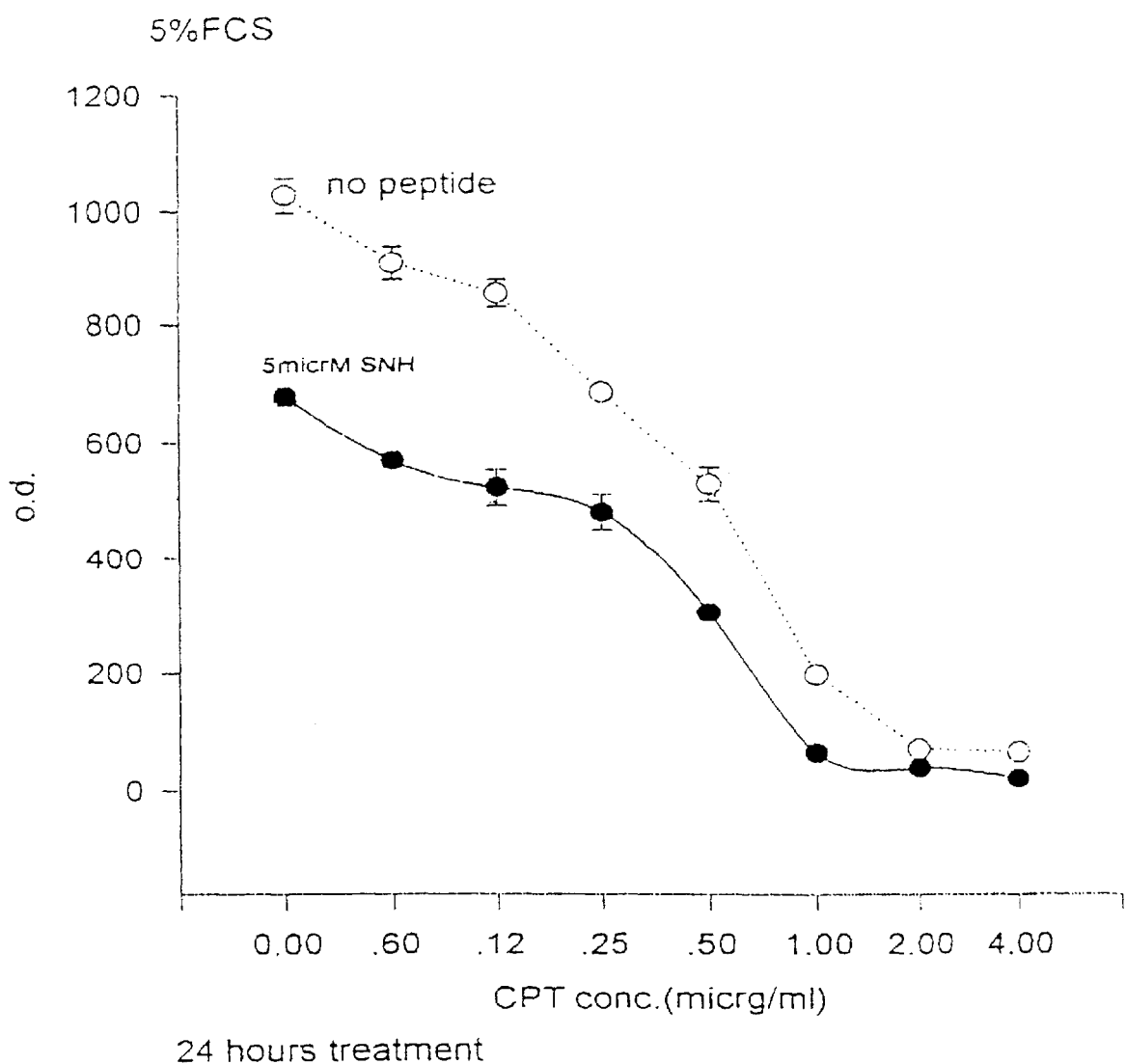
FIG. 10 illustrates a dose response curve in CT-26 cell line (murine colon cancer) using the combination therapy of SNH and CPT-11.
Figure 11:
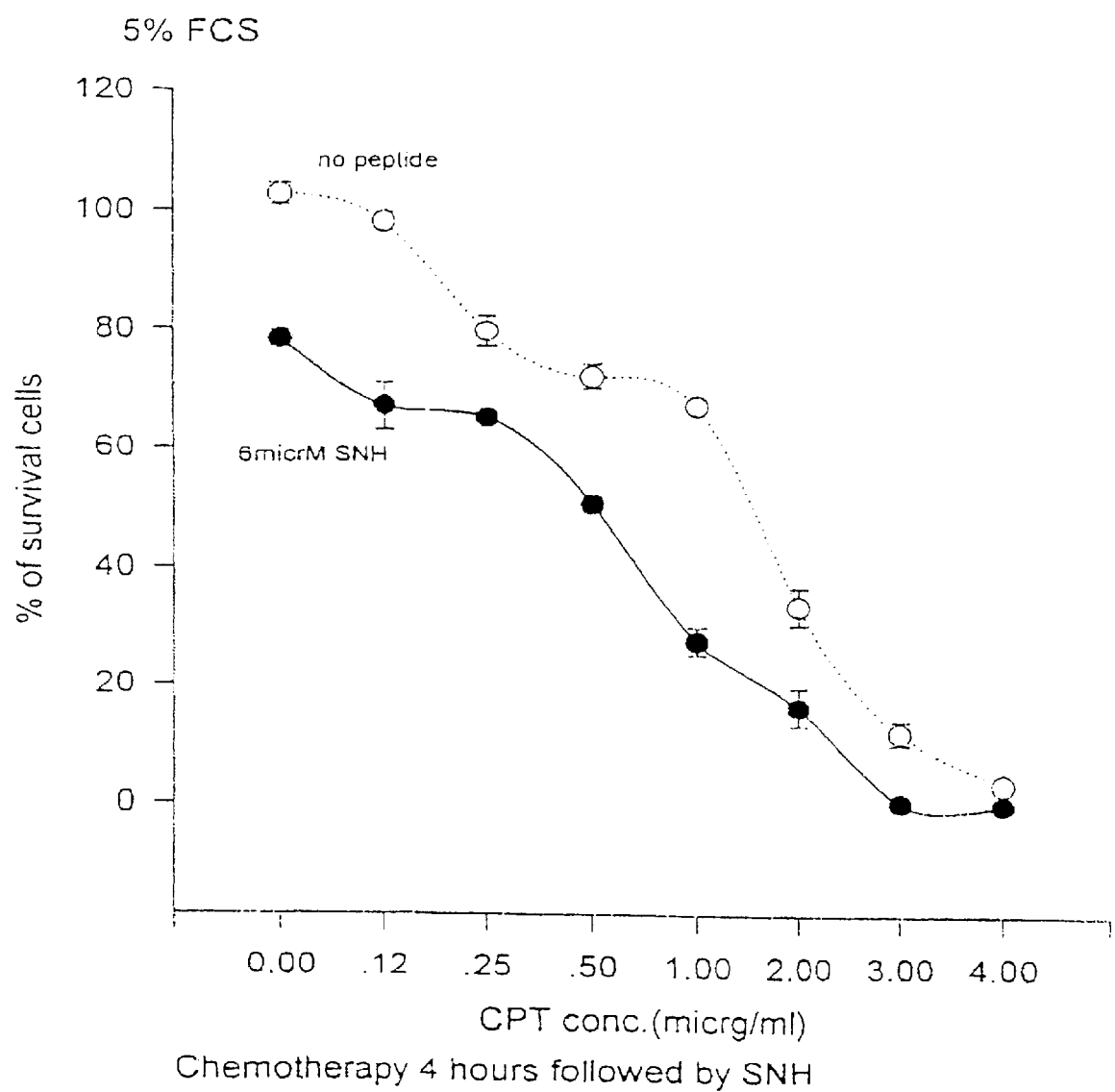
FIG. 11 illustrates a dose response curve in HT-29 cell line (human colon cancer) using the combination therapy of SNH and CPT-11.

FIGS. 4 and 5 show the synergistic effect of cisplatin (alkylating agent) and SNH and navebine (anti-microtubule) and SNH, respectively. Five micromolar SNH reduced the $IC_{50}$ of cisplatin by 4-fold and of navelbine, by at least 2-fold. In the case of doxorubicine (antibiotic), the effect was less pronounced (see, FIG. 6) and was only additive in the case of gemcitabine (anti-metabolite, see, FIG. 7). In the case of CPT-11 (irinotecan, a topoisomerase I inhibitor), the SNH effect was synergistic with 5 μM SNH reducing the $IC_{50}$ by at least two-fold (see, FIG. 8). The combination with Taxol was very effective (see, FIG. 9). An enhancing effect was also observed with CT-26 (a murine colon cancer) and with HT-29 (a human colon cancer cell line) (see, FIGS. 10 and 11, respectively).

Using different schedules of treatment, the synergistic effect of the combination was preserved. For example, with HT-29 it was shown that a 4 hour treatment with SNH, followed by a 24 hour treatment with the antagonist was also effective (see, FIG. 11). In another experiment (see, FIG. 3), 8 μM SNH were added to NCI-H727 cells (after a culturing period of 24 h) for an incubation of 2 h followed by Taxol addition (0.003–1 μg/ml, (closed circles) for an additional 4 h incubation period. The drugs were then removed and replaced by fresh medium for another 66 h. Results showed that SNH addition reduced the $IC_{50}$ of Taxol (anti-microtubule agent) by about 6-fold, indicating a synergistic effect.

Example 5

This example illustrates expression of VPAC1 receptor in NCI-H727, a receptor that has been associated before with tumor growth A. RNA Extraction Total RNA from cultured cells was extracted by RNAzol B reagent (Biotec, TX, USA) according to the manufacturer's protocol. Briefly, cells grown on 100 mm Petri dishes in 10% FCS supplemented RPMI were dissolved in 5 ml RNAzol reagent. Cells were then collected, 0.1 volume of chloroform was added, and the mixture was centrifuged (15 min at 12,000 ×g). The upper aqueous phase was transferred to a fresh tube, equal volume of isopropanol was then added, mixed and centrifuged (10 min at 12,000 ×g). The pellet was washed twice by 70% ethanol, dissolved in 1/10 vol 3M Na Acetate and 2.5 vol EtOH, and stored at −20° C.

B. RT-PCR

Complementary DNA was first obtained by reverse transcription of 2 μg total RNA with M-MLV reverse transcriptase (200 U, Gibco-BRL) using random hexamers as primers (1 h at 37° C., 5 min 95° C.). This reaction was followed by 30–45 PCR amplification cycles using Red Hot DNA polymerase (5 U, Advanced Biotechnologies, Surrey, UK) (1 min 94° C., primer annealing at 60° C. for 1 min, extension at 72° C for 1 min) using thermocycler (MJ Research). In order to control RNA quantity of different samples 2 μl samples of cDNA were amplified in parallel to the test primers with specific primers for the human glyceraldehyde 3-phosphate dehydrogenase (GAPDH). Specific primers for the various VIP receptors (e.g., Usdin, T. B. et al., *Endocrinology* 135:2662–80 (1994), (Sreedharan, S. P. et al, *Proc. Natl. Acad. Sci. USA* 92:2939–43 (1995), and as reviewed in Harmar, A. J. et al., *Pharmacological Reviews* 50:265–270 (1998)) are outlined in Table 1. Specific primers for VIP mRNA (Itoh, N. et al., *Nature* 304:547–549 (1983), Bodner, M. et al. *Proc Natl Acad Sci USA* 82:3548–51 (1985)) are outlined also in Table 1. PCR products were subjected to electrophoresis on a 2% Nusieve GTG agarose gel (FMC Bioproducts, ME, USA) stained with ethidium bromide and visualized by UV light.

RT-PCR data indicate expression of VPAC1 receptor in NCI-H727, a receptor that has been associated before with tumor growth (see, Sreedharan, S. P. et al., *Proc. Natl. Acad. Sci. USA* 92:2939–43 (1995)).

Example 6

This example illustrates the ability of VIP receptor antagonists to alter the growth of breast cancer cells was investigated in vitro.

The ability of VIP receptor antagonists to alter the growth of breast cancer cells was investigated in vitro using the MTT colorimetric. The semiautomated MTT assay measures reduction of a tetrazolium compound by tumor cells to formazan. The optical density at 570 nm was determined for 8 wells at each inhibitor concentration. Seeding densities were 5×104 cells/well and cells were grown in 96 well plates for 5 days.

Table 3 shows that VIPhyb inhibited MCF-7 proliferation in a concentration dependent manner in a MTT assay, VIPhyb at a 10 μM significantly inhibited MCF-7 proliferation. (SN) VIPhyb was a more potent inhibitor than VIPhyb, it was tested in the NCI "compare analysis" using a panel of 56 cancer cell lines. (SN)VIPhyb significantly inhibited the proliferation of 51 of 56 cell lines tested including 6/6 leukemia, 7/7 non-small cell lung cancer, 6/7 colon cancer, 5/5 CNS cancer, 8/8 melanoma, 5/6 ovarian cancer, 6/7 renal cancer, 2/2 prostate cancer and 6/8 breast cancer cell lines (Table 3 legend).

TABLE 3

VIPhyb Inhibited MCF-7 Proliferation

| Addition | Absorbance at 570 nM |
|---|---|
| None | .406 ± .065 |
| ViPhyb, 1 μM | .417 ± .064 |
| ViPhyb 3 μM | .353 ± .048 |
| ViPhyb 10 μM | .317 ± .030* |
| VIPhyb + VIP 1 μM | .315 ± .040* |
| ViPhyb VIP 10 μM | .382 ± .036 |
| VIP, 1 μM | .368 ± .028 |
| VIP, 10 μM | .420 ± .051 |

The mean value±S. D. of 8 determinations is indicated; *, p<0.05 using student's t-test. (SN)VIPhyb inhibited the growth of leukemia (CCRF-CEM), HL-60(TB), K-562, MOLT-4, RPMI-8226, SR), non-small cell lung cancer (A549, EKVX, HOP-62, HOP-92, H23, H322M, H460 and H522), colon cancer (COLO205, HCC-2998, HCT-116, HT29, KM12, SW-620), CNS cancer (SF-268, SF-295, SF-539, SNB-19, U251), melanoma (LOX IMVI, MALME-3M, M14, SK-MEL-2, SK-MEL-28, SK-MEL-5, UACC-257, UACC-62), ovarian cancer (IGROV1, OVCAR-3, OVCAR-5, OVCAR-8, SK-OV-3), renal cancer (786-0, A498, CAKI-1, RXF 393, SM12C, TK-l0), prostate cancer (PC-3, DU-145) and breast cancer (MCF-7, MDA-MB-231, HS 578T, MDA-MB-435, MDA-N and T-47D).

Example 7

This example illustrates the proliferative aspects of VIPhybrid analogs in vivo.

To test the proliferative aspects of VIPhybrid analogs in vivo, nude mice bearing breast cancer xenografts were utilized. Female athymic Balb/c nude mice, 4–5 weeks old, were housed in a pathogen-free temperature controlled isolation room and the diet consisted of autoclaved rodent chow and autoclaved water given ad libitum. MDA-MB231 cells ($1 \times 10^7$) were injected into the right flank of each mouse subcutaneously. Palpable tumors were observed in approximately 90% of the mice after 2 weeks. PBS (100 μl) or VIPhyb analogs (10 μg/day) were injected subcutaneously adjacent to the tumor. Taxol was injected once (1.5 mg i.p.) after 2 weeks. The tumor volume (height×width×depth) was determined twice weekly by calipers and recorded.

Figure 12:
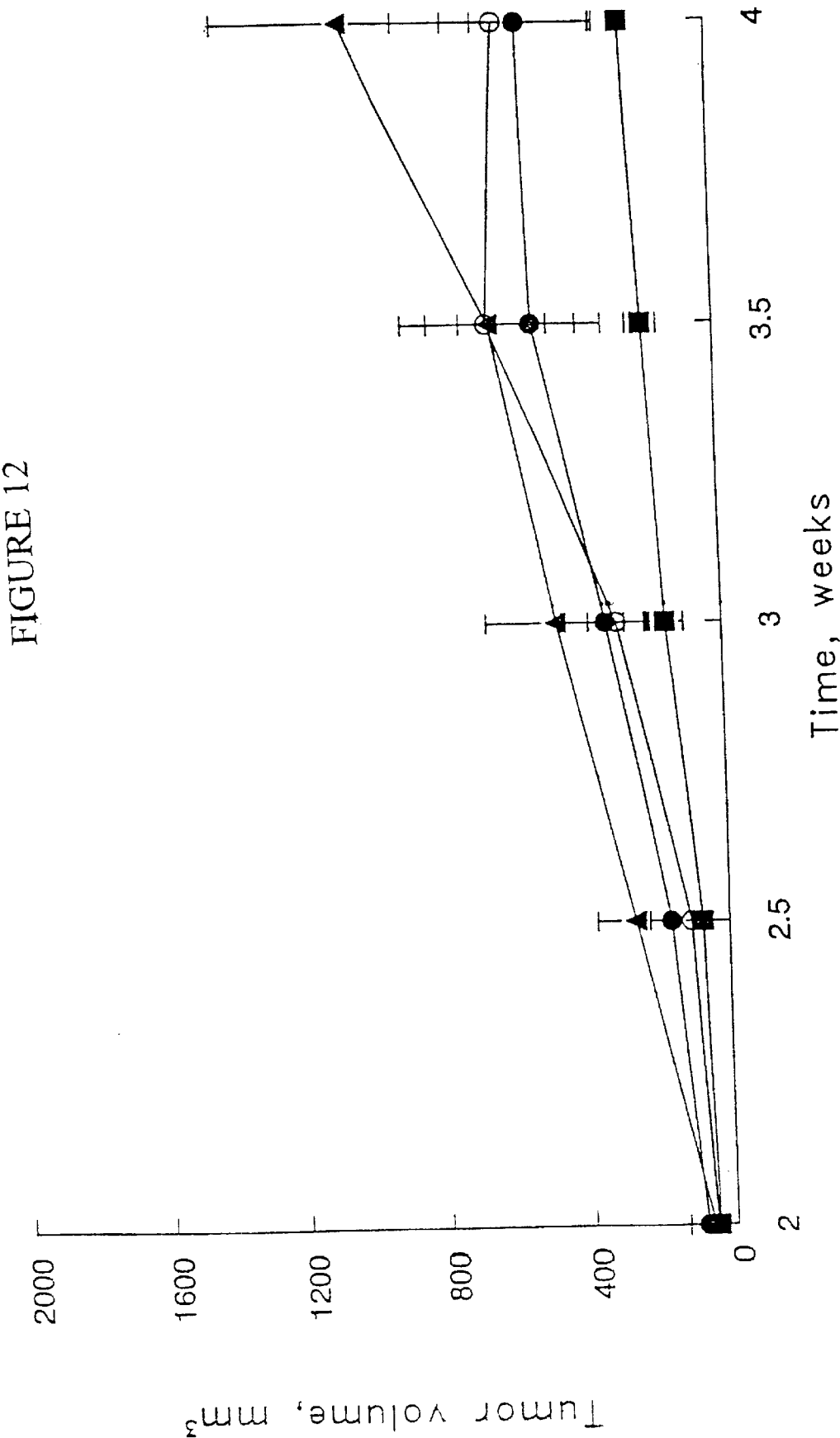
FIG. 12 illustrates in vivo use of a composition of the present invention on MDA-MB231 xenografts in nude mice. A palpable mass formed after 1 week and animals were subsequently injected with 100 $\mu$l of PBS daily s.c. (▲), 10 $\mu$g of VIPhyb daily s.c. (●), 1.5 mg Taxol i.p. (○), and 10 $\mu$g of VIPhyb s.c. daily +1.5 mg Taxol i.p. (■); p<0.05, *. The mean value±S.D. of 5 determinations is indicated.

FIG. 12 shows that small tumors formed after 2 weeks in all mice. In control mice injected wit PBS the xenografts grew exponentially and large tumors (1121 mm$^3$) were present after 4 weeks. In animals injected with VIPhyb or Taxol the tumors were smaller in size 508 and 613 mm$^3$ respectively). In animals injected with VIPhyb and Taxol the tumors were significantly smaller in size (234 mm$^3$). These results suggest that Taxol+VIPhyb synergistically inhibit xenograft growth in vivo.

All publications, patents and patent applications mentioned in this specification are herein incorporated by reference into the specification to the same extent as if each individual publication, patent or patent application was specifically and individually indicated to be incorporated herein by reference. Although the foregoing invention has been described in some detail by way of illustration and example for purposes of clarity of understanding, it will be obvious that certain changes and modifications may be practiced within the scope of the appended claims.

What is claimed is:

1. A pharmaceutical composition comprising:

a) a vasoactive intestinal polypeptide (VIP) antagonist, said VIP antagonist comprising the following amino acid sequence:

$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$ wherein:

$R^1$ and $R^2$ are independently members selected from the group consisting of hydrogen, $C_1$ to $C_{20}$ alkyl and $C_1$ to $C_{20}$ acyl, provided that at least one of $R^1$ or $R^2$ is hydrogen; and $X^1$ and $X^2$ are independently members selected from the group consisting of naturally occurring amino acids, amino acid analogs, and amino acid mimetics (SEQ ID NO:1);

with the proviso that said VIP antagonist does not have the following amino acid sequence:

Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6);

b) a chemotherapeutic agent; and c) a pharmaceutically acceptable carrier.

2. The pharmaceutical composition in accordance with claim 1, wherein $X^1$ and $X^2$ are members independently selected from the group consisting of naturally occurring amino acids, amino acid analogs and amino acid mimetics of hydrophobic character.

3. The pharmaceutical composition in accordance with claim 1, wherein $R^1$ is H; $R^2$ is H; $X^1$ is a norleucine residue; and $X^2$ is a valine residue (SEQ ID NO:2).

4. The pharmaceutical composition in accordance with claim 1, wherein $R^1$ is $CH_3(CH_2)_{16}CO$—; $R^2$ is H; $X^1$ is a norleucine residue; and $X^2$ is a valine residue (SEQ ID NO:3).

5. The pharmaceutical composition in accordance with claim 1, wherein $R^1$ is $CH_3(CH_2)_{16}CO$—; $R^2$ is H; $X^1$ is a methionine residue; and $X^2$ is a valine residue (SEQ ID NO:4).

6. The pharmaceutical composition in accordance with claim 1, wherein said chemotherapeutic agent is a member selected from the group consisting of platinum coordination compounds, topoisomerase inhibitors, antibiotics, antimitotic alkaloids and difluoronucleosides.

7. The pharmaceutical composition in accordance with claim 6, wherein said chemotherapeutic agent is a platinum coordination compound.

8. The pharmaceutical composition in accordance with claim 7, wherein said platinum coordination compound is a member selected from the group consisting of cisplatin, cis-diamminediaquoplatinum (II)-ion, chloro(diethylenetriamine)-platinum(II)chloride, dichloro(ethylenediamine)-platinum(II), carboplatin, spiroplatin, iproplatin, diammine(2-ethylmalonato)-platinum(II), ethylenediaminemalonatoplatinum(II), aqua(1,2-diaminodyclohexane)-sulfatoplatinum(II), (1,2-diaminocyclohexane)malonatoplatinum(II), (4-caroxyphthalato)(1,2-diaminocyclohexane)platinum(II), (1,2-diaminocyclohexane)-(isocitrato)platinum(II), (1,2-diaminocyclohexane)cis(pyruvato)platinum(II); (1,2-diaminocyclohexane)oxalatoplatinum(II), ormaplatin and tetraplatin.

9. The pharmaceutical composition in accordance with claim 8, wherein said platinum coordination compound is cisplatin.

10. The pharmaceutical composition in accordance with claim 6, wherein said chemotherapeutic agent is a topoisomerase inhibitor.

11. The pharmaceutical composition in accordance with claim 10, wherein said topoisomerase is a member selected from the group consisting of topotecan, irinotecan and 9-aminocamptothecin.

12. The pharmaceutical composition in accordance with claim 11, wherein said topoisomerase is irinotecan.

13. The pharmaceutical composition in accordance with claim 6, wherein said chemotherapeutic agent is an antibiotic.

14. The pharmaceutical composition in accordance with claim 13, wherein said antibiotic is a member selected from the group consisting of doxorubicin, mitomycin, bleomycin, daunorubicin and streptozocin.

15. The pharmaceutical composition in accordance with claim 14, wherein said antibiotic is doxorubicin.

16. The pharmaceutical composition in accordance with claim 6, wherein said chemotherapeutic agent is an antimitotic alkaloid.

17. The pharmaceutical composition in accordance with claim 16, wherein said antimitotic alkaloid is a member selected from the group consisting of vinorelbine, vinblastine, vincristine, Taxol and vindesine.

18. The pharmaceutical composition in accordance with claim 17, wherein said antimitotic alkaloid is vinorelbine.

19. The pharmaceutical composition in accordance with claim 6, wherein said chemotherapeutic agent is a difluoronucleoside.

20. The pharmaceutical composition in accordance with claim 19, wherein said difluoronucleoside is gemcitabine.

21. A method of inhibiting the growth of a tumor cell, said method comprising:
contacting said tumor cell with an effective amount of a chemotherapeutic agent and a vasoactive intestinal polypeptide (VIP) antagonist, said VIP antagonist comprising the following amino acid sequence:
$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$;
wherein:
$R^1$ and $R^2$ are members independently selected from the group consisting of hydrogen, $C_1$ to $C_{20}$ alkyl and $C_1$ to $C_{20}$ acyl, provided that at least one of $R^1$ or $R^2$ is hydrogen; and
$X^1$ and $X^2$ are members independently selected from the group consisting of naturally occurring amino acids, and amino acid mimetics (SEQ ID NO1);
with the proviso that said antagonist is not have the following amino acid sequence:
Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO:6).

22. The method of inhibiting the growth of tumor cells in accordance with claim 21, wherein said vasoactive intestinal polypeptide (VIP) antagonist and said chemotherapeutic agent contact said tumor cell simultaneously.

23. The method of inhibiting the growth of tumor cells in accordance with claim 21, wherein $R^1$ is $CH_3(CH_2)_{16}CO$—; $R^2$ is H; $X^1$ is a norleucine residue; and $X^2$ is a valine residue (SEQ ID NO:3).

24. The method of inhibiting the growth of tumor cells in accordance with claim 21, wherein said chemotherapeutic agent is a member selected from the group consisting of platinum coordination compounds, topoisomerase inhibitors, antibiotics, antimitotic alkaloids and difluoronucleosides.

25. The method of inhibiting the growth of tumor cells in accordance with claim 24, wherein said platinum coordination is cisplatin.

26. The method of inhibiting the growth of tumor cells in accordance with claim 24, wherein said topoisomerase is irinotecan.

27. The method of inhibiting the growth of tumor cells in accordance with claim 24, wherein said antibiotic is doxorubicin.

28. The method of inhibiting the growth of tumor cells in accordance with claim 24, wherein said antimitotic alkaloid is vinorelbine.

29. The method of inhibiting the growth of tumor cells in accordance with claim 24, wherein said difluoronucleoside is gemcitabine.

30. The method of inhibiting the growth of tumor cells in accordance with claim 21, wherein said tumor cell is selected from the group consisting of lung, colon, breast, ovarian, prostate and hepatic cells.

31. The method of inhibiting the growth of tumor cells in accordance with claim 21, wherein said chemotherapeutic agent and said VIP antagonist are formulated in a pharmaceutically acceptable form with an excipient or carrier.

32. The method of inhibiting the growth of tumor cells in accordance with claim 21, further comprising the step of observing for a reduction in the growth of said tumor cell.

33. A method of inhibiting the growth of a tumor cell in a mammalian subject, said method comprising:
administering to said subject an effective amount of combination of a chemotherapeutic agent and a vasoactive intestinal polypeptide (VIP) antagonist, said VIP antagonist comprising the following amino acid sequence:
$R^1$-Lys-Pro-Arg-Arg-Pro-Tyr-Thr-Asp-Asn-Tyr-Thr-Arg-Leu-Arg-Lys-Gln-$X^1$-Ala-$X^2$-Lys-Lys-Tyr-Leu-Asn-Ser-Ile-Leu-AsnNH-$R^2$;
wherein:
$R^1$ and $R^2$ are members independently selected from the group consisting of hydrogen, $C_1$ to $C_{20}$ alkyl and $C_1$ to $C_{20}$ acyl, provided
wherein that at least one of $R^1$ or $R^2$ is hydrogen;
$X^1$ and $X^2$ are members independently selected from the group consisting of naturally occurring amino acids, amino acid analogs and amino acid mimetics (SEQ ID NO:1);
with the proviso that said antagonist is not have the following amino acid sequence:
Lys-Pro-Arg-Arg-Pro-Tyr-Thr-Asp-Asn-Tyr-Thr-Arg-Leu-Arg- Lys-Gln-Met-Ala-Val-Lys-Lys-Tyr-Leu-Asn-Ser-Ile-Leu-Asn (SEQ ID NO:6).

34. The method of inhibiting the growth of tumor cells in accordance with claim 33, wherein said vasoactive intestinal polypeptide (VIP) antagonist and said chemotherapeutic agent are administered simultaneously.

35. The method of inhibiting the growth of tumor cells in accordance with claim 33, wherein $R^1$ is $CH_3(CH_2)_{16}CO$—; $R^2$ is H; $X^1$ is a norleucine residue; and $X^2$ is a valine residue (SEQ ID NO:3).

36. The method of inhibiting the growth of tumor cells in accordance with claim 33, wherein said mammalian subject is a human being.

37. The method of inhibiting the growth of tumor cells in accordance with claim 33, wherein said chemotherapeutic agent is a member selected from the group consisting of platinum coordination compounds, topoisomerase inhibitors, antibiotics, antimitotic alkaloids and difluoronucleosides.

38. The method of inhibiting the growth of tumor cells in accordance with claim 37, wherein said platinum coordination is cisplatin.

39. The method of inhibiting the growth of tumor cells in accordance with claim 37, wherein said topoisomerase is irinotecan.

40. The method of inhibiting the growth of tumor cells in accordance with claim 37, wherein said antibiotic is doxorubicin.

41. The method of inhibiting the growth of tumor cells in accordance with claim 37, wherein said antimitotic alkaloid is vinorelbine.

42. The method of inhibiting the growth of tumor cells in accordance with claim 37, wherein said difluoronucleoside is gemcitabine.

43. The method of inhibiting the growth of tumor cells in accordance with claim 33, wherein said tumor cell is selected from the group consisting of lung, colon, breast, ovarian, prostate and hepatic cells.

44. The method of inhibiting the growth of tumor cells in accordance with claim 33, wherein said chemotherapeutic agent and said VIP antagonist are formulated in a pharmaceutically acceptable form with an excipient or carrier.

45. The method of inhibiting the growth of tumor cells in accordance with claim 33, further comprising the step of observing for a reduction in the growth of said tumor cell.

46. A method of manufacturing a medicament for inhibiting growth of a tumor cell or for the treatment of cancer wherein a composition of claim 1 is used.

47. A method of manufacturing a medicament for inhibition growth of a tumor cell in a patient wherein said tumor cell is a member selected from the group consisting of lung, colon, breast, ovarian, prostate and hepatic cells and wherein a composition of claim 1 is used.

* * * * *